(12) United States Patent
Kapur

(10) Patent No.: US 8,518,906 B2
(45) Date of Patent: Aug. 27, 2013

(54) RHO KINASE INHIBITORS FOR TREATMENT OF MASTOCYTOSIS AND ACUTE MYELOID LEUKEMIA

(75) Inventor: Reuben Kapur, Zionsville, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 13/586,233

(22) Filed: Aug. 15, 2012

(65) Prior Publication Data

US 2013/0046009 A1  Feb. 21, 2013

Related U.S. Application Data

(60) Provisional application No. 61/524,993, filed on Aug. 18, 2011.

(51) Int. Cl.
*C12N 15/11* (2006.01)
*C12Q 1/68* (2006.01)

(52) U.S. Cl.
USPC ........................................ 514/44 A; 435/6.14

(58) Field of Classification Search
None
See application file for complete search history.

(56) References Cited

U.S. PATENT DOCUMENTS 6,153,600 A     11/2000  Leder et al.
2009/0325905 A1*  12/2009  Peterson et al. ............... 514/89

OTHER PUBLICATIONS

Mali et al, Rho Kinase Inhibitors as Potential Therapeutic Agents for Oncogenic KIT, FLT3, and BCR-ABL Induced Leukemogenesis, Nov. 2009, Blood, vol. 114, No. 22, abstract 3909.*
Demetri et al., "Efficacy and safety of imatinib mesylate in advanced gastrointestinal stromal tumors," N. Engl. J. Med. 347(7):472-480 (2002).
Frost et al., "Juxtamembrane mutant V560GKit is more sensitive to Imatinib (STI571) compared with wild-type c-kit whereas the kinase domain mutant D816VKit is resistant," Mol. Cancer Ther. 1:1115-1124 (2002).
Jacobs et al., "The structure of dimeric ROCK I reveals the mechanism for ligand selectivity," J. Biol. Chem. 281 (1):260-268 (2006).
Lochhead et al., "Activating ROCK1 somatic mutations in human cancer," Oncogene 29:2591-2598 (2010).
Ma et al., "The c-KIT mutation causing human mastocytosis is resistant to STI571 and other KIT kinase inhibitors; kinases with enzymatic site mutations show different inhibitor sensitivity profiles that wild-type kinases and those with regulatory-type mutations," Blood 99:1741-1744 (2002).
Sahai and Marshall, "RHO-GTPases and cancer," Nat. Rev. Cancer 2:133:142 (2002).
Shibuya et al., "Effects of fasudil in acute ischemic stroke: results of a prospective placebo-controlled double-blind trial," J. Neurol. Sci. 238:31-39 (2005).

* cited by examiner

*Primary Examiner* — Tracy Vivlemore
*Assistant Examiner* — Kate Poliakova
(74) *Attorney, Agent, or Firm* — Armstrong Teasdale LLP

(57) ABSTRACT

The disclosure is directed to methods of treating hematologic malignancies. More particularly, the disclosure is directed to methods of treating hematologic malignancies using Rho kinase (ROCK) inhibitors and myosin light chain-specific inhibitory RNA molecules. The disclosure is further directed to methods of identifying drug candidates for inhibiting ROCK in hematologic malignancies.

4 Claims, 26 Drawing Sheets
(1 of 26 Drawing Sheet(s) Filed in Color)

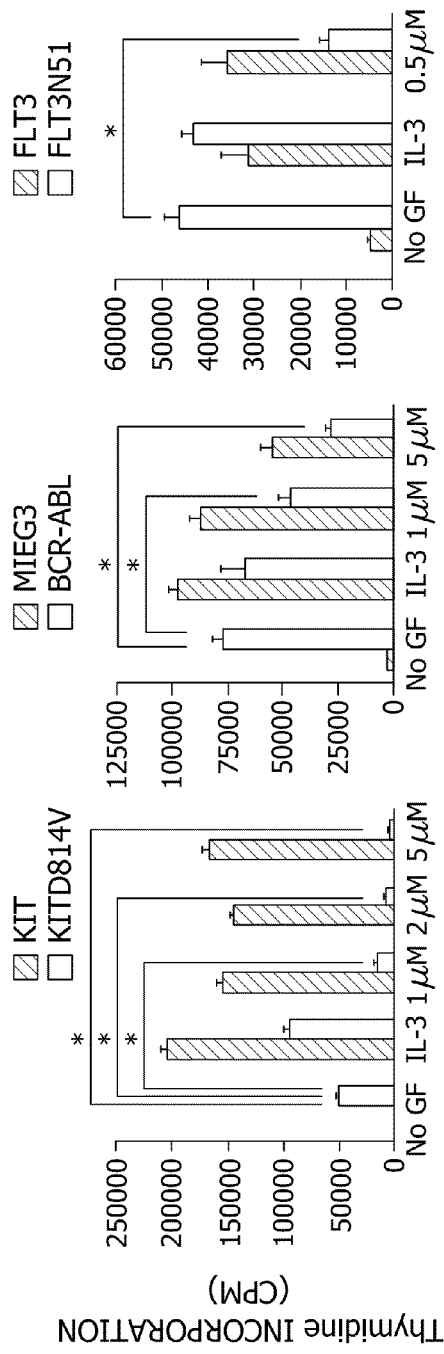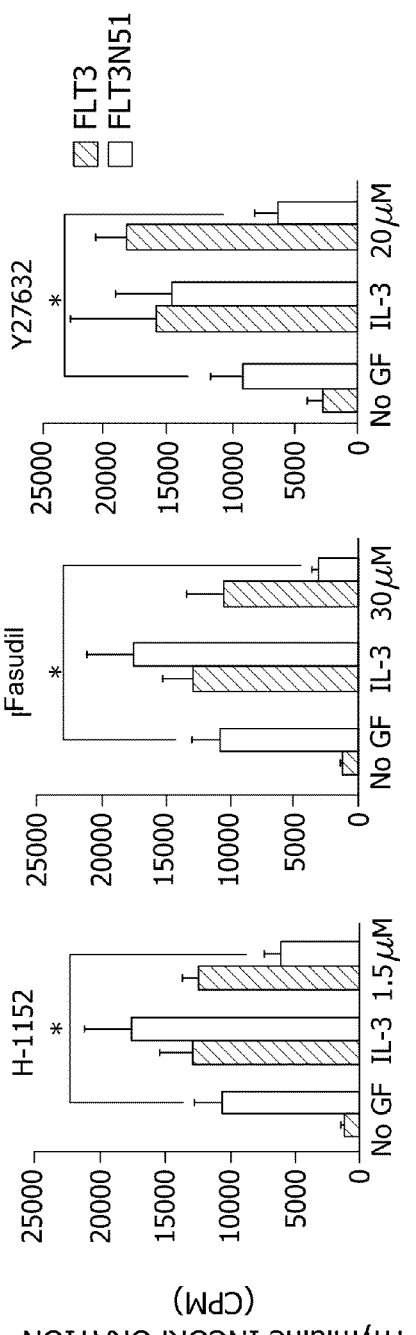
FIG. 2A
FIG. 2B

RHO KINASE INHIBITORS FOR TREATMENT OF MASTOCYTOSIS AND ACUTE MYELOID LEUKEMIA

CROSS-REFERENCE TO RELATED APPLICATIONS

This application claims priority to provisional patent application No. 61/524,993, filed on Aug. 18, 2011, which is incorporated herein by reference in its entirety.

STATEMENT REGARDING FEDERALLY SPONSORED RESEARCH

This invention was made with government support under R01 HL075816-06, R01 HL077177-04, and R01 HL081111-04 awarded by the National Institutes of Health. The government has certain rights in the invention.

INCORPORATION OF SEQUENCE LISTING

A paper copy of the Sequence Listing and a computer readable form of the sequence containing the file named "31377-5 (IURTC 12023)_ST25.txt", which is 837 bytes in size (as measured in MS-DOS), are provided herein and are herein incorporated by reference. This Sequence Listing consists of SEQ ID NOs: 1-3.

BACKGROUND OF THE DISCLOSURE

The present disclosure relates generally to the treatment of hematologic malignancies. More particularly, the present disclosure relates to the treatment of hematologic malignancies using Rho kinase inhibitors.

Hematologic malignancies are types of cancer affecting blood, bone marrow, and lymph nodes. Hematologic malignancies may be derived from either the myeloid blood cell lineage or the lymphoid blood cell lineage. Current treatments may involve chemotherapy, radiotherapy, immunotherapy, blood transfusions, and bone marrow transplants.

Alternative treatment approaches are directed to developing less toxic and more efficacious therapies. Molecules that are either mutated or hyperactivated as a result of specific mutations in hematologic malignancies may present alternatives for targeting therapies. For example, mutations have been identified in signaling molecules that may contribute to myeloproliferative disease (MPD), acute myeloid leukemia (AML), and chronic myeloid leukemia (CML). For example, mutations have been identified in KIT (tyrosine-protein kinase Kit or CD117) in systemic mastocytosis (SM), gastrointestinal stromal tumors (GISTs), and in core binding factor acute myeloid leukemia (CBF-AML). FLT3 (Fms-like tyrosine kinase 3 or cluster of differentiation antigen 135) internal tandem duplications (FLT3-ITD) have been identified in AML. BCR-ABL translocations (breakpoint cluster region-V-abl Abelson murine leukemia viral oncogene homolog 1 fusion) have been identified in chronic myelogenous leukemia (CML).

Oncogenic KIT, for example, is constitutively phosphorylated and demonstrates ligand-independent proliferation when expressed in cell lines or primary bone marrow cells. Although mutations within the juxtamembrane region of KIT in GIST are sensitive to inhibition by imatinib mesylate, other KIT mutations, such as KITD816V, within the tyrosine kinase domain, are imatinib-resistant. Similar to KIT, FLT3 is another member of the class III subfamily of receptor tyrosine kinase. FLT3 mutations are one of the most frequent somatic alterations in AML occurring in approximately one third of these patients and predict poor prognosis. FLT3-ITD mutations also result in ligand-independent constitutive activation of the receptor's tyrosine kinase activity. Several FLT3 inhibitors have been described, but they vary considerably with respect to selectivity for FLT3. Similarly, nearly all patients with CML express the BCR-ABL fusion protein and the expression of BCR-ABL in stem cells is sufficient to induce CML. Although imatinib has been used successfully to treat CML, emergence of BCR-ABL positive residual stem cells and imatinib-resistant BCR-ABL mutants has resulted in drug resistance and relapse related concerns with this disease. Thus, the identification of new targets contributing to the initiation and/or progression of multiple hematologic malignancies involving activated tyrosine kinases may be of therapeutic benefit.

Rho kinases and Rho-associated coiled coil-containing protein kinases (ROCK) are protein serine/threonine kinases. Two isoforms of ROCK have been described that are encoded by two separate genes, ROCK1 and ROCK2. ROCK1 and ROCK2 share close to 65% overall sequence homology at the protein level and nearly 92% sequence homology of their kinase domains. Activation of ROCK by GTP bound Rho or by lipid mediators leads to the phosphorylation of various downstream target proteins including myosin phosphatase, myosin light chain (MLC) and LIM kinases 1 and 2. Activation of these substrates results in the recruitment of mediators of actin polymerization and formation of focal adhesions leading to changes in growth, survival and cell motility.

Emerging data suggests that ROCK may be an oncogene. For example, cancer genome sequencing revealed three ROCK1 activating mutations in primary human breast cancer cells and in human non-small-cell lung carcinoma line NCI-H1770. Introducing these mutants into fibroblasts elevated ROCK activity, which lead to changes in the actin cytoskeleton, increased motility and decreased cell adhesion. While ROCK may play a role in solid tumors, its role in regulating growth, survival and transformation downstream of tyrosine kinases involved in SM, AML or CML is unknown.

Although 70-80% AML patients go into remission with standard cytotoxic therapy, most relapse and are unresponsive to subsequent therapies. Both AML and myeloproliferative disease (MPD) increase in incidence dramatically in the aging population. Unfortunately, elderly patients fare worse than younger patients as a result of co-morbidities. Additionally, signaling molecules associated with hematologic malignancies may present alternatives for targeting therapies. Accordingly, there exists a need to develop alternative treatments with increased efficacy and reduced toxicity for these diseases.

SUMMARY OF THE DISCLOSURE

The present disclosure relates generally to methods for treating hematologic malignancies. More particularly, the present disclosure relates to methods for treating hematologic malignancies by administering ROCK inhibitors. The present disclosure further relates to methods for identifying a drug candidate for inhibiting ROCK in hematologic malignancies.

In one aspect, the present disclosure is directed to a method of treating a hematologic malignancy, the method comprising administering a therapeutically effective amount of a Rho kinase (ROCK) inhibitor.

In another aspect, the present disclosure is directed to a method of treating a hematologic malignancy, the method comprising administering a myosin light chain-specific inhibitory RNA molecule of SEQ ID NO: 1.

In another aspect, the present disclosure is directed to a method of identifying a drug candidate for inhibiting ROCK in a hematologic malignancy. The method includes culturing a first cell expressing an oncogene selected from the group consisting of ROCK, KIT, FLT3, BCR-ABL, MLL-AF9 and MPLW515L; culturing a second cell expressing an oncogene selected from the group consisting of ROCK, KIT, FLT3, BCR-ABL, MLL-AF9 and MPLW515L; contacting the drug candidate with the first cell; measuring ROCK activity of the first cell after contacting with the drug candidate; measuring ROCK activity of the second cell, wherein the second cell is not contacted with the drug candidate; and comparing the ROCK activity of the first cell with the ROCK activity of the second cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 2A are graphs showing thymidine incorporation in cells expressing KIT, MIEG3, FLT3, KITD814V, BCR-ABL, or FLT3N51 in the presence of the growth factor IL-3 as described in Example 2.

FIG. 2B are graphs showing thymidine incorporation in cells expressing FLT3 or FLT3N51 in the presence of the growth factor IL-3 and treated with H-1152, fasudil, and Y27632 as described in Example 2.

Figure 1:
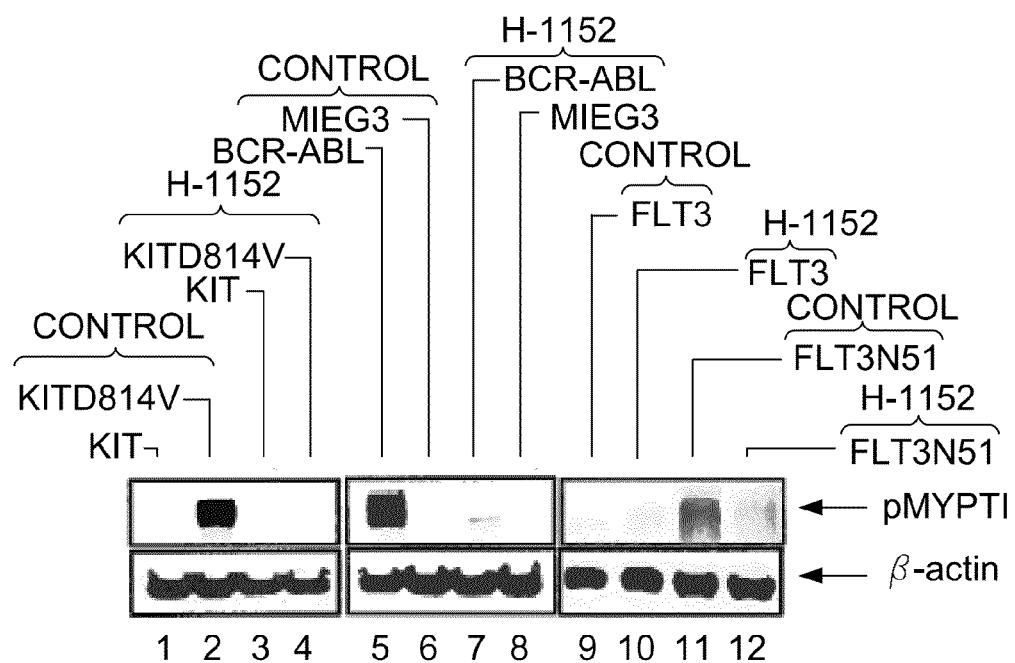
FIG. 1 is a Western blot assessing the phosphorylation of myosin phosphatase (pMYPT1) by ROCK in the presence or absence of H-1152 as described in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, signaling molecules have been identified that are associated with hematologic malignancies, and thus, represent targets for therapies for hematologic malignancies. More particularly, methods have been discovered that allow for the treatment of hematologic malignancies. In many embodiments, the methods may be used to treat hematologic malignancies such as, for example, systemic mastocytosis, gastrointestinal stromal tumors, core binding factor acute myeloid leukemia, myeloproliferative disease, acute myeloid leukemia, acute megakaryocytic leukemia and chronic myeloid leukemia. Thus, the methods may be used to halt, slow and/or reverse the onset or progression of hematologic malignancies in individuals. The methods include administration of a Rho kinase inhibitor to an individual in need thereof specifically afflicted with a hematologic malignancy or at risk of developing a hematologic malignancy due to heredity or other factors (e.g., experimental induction). As such, in some embodiments, the methods disclosed herein are directed to a subset of the general population, including experimental animals, such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain diseases or conditions.

Particularly suitable individuals may be humans having a hematologic malignancy or at risk of developing a hematologic malignancy due to heredity, life cycle, age or other factors. Other suitable individuals may be experimental animals such as, for example, mice, rats, pigs, dogs, sheep and non-human primates.

Methods of Treating Hematologic Malignancies

In one aspect, the present disclosure is directed to a method of treating a hematologic malignancy in an individual in need thereof The method includes administering a therapeutically effective amount of a Rho kinase (ROCK) inhibitor. As used herein, the terms "therapeutically effective amount", "effective amount", and "effective" are intended to designate a dose that causes a relief of symptoms of a disease or condition as noted through clinical testing and evaluation, individual observation, and/or the like, and/or a dose that causes a detectable change in biological or chemical activity. The detectable changes may be detected and/or further quantified by those skilled in the art for the relevant mechanism or process. As is generally understood in the art, the dosage will vary depending on the administration routes, symptoms and body weight of the individual and may also depend upon the compound being administered.

Hematologic malignancies may be types of cancers affecting blood, bone marrow, and lymph nodes. Hematologic malignancies may be derived from either the myeloid blood cell lineage or the lymphoid blood cell lineage. Hematologic malignancies particularly suitable for treatment by administering a ROCK inhibitor may be, for example, systemic mastocytosis, gastrointestinal stromal tumors, core binding factor acute myeloid leukemia, myeloproliferative disease, acute myeloid leukemia, acute megakaryocytic leukemia and chronic myeloid leukemia.

Treatment of hematologic malignancies is by administering a ROCK inhibitor. As used herein, "treatment" refers to the administration or application of a ROCK inhibitor to an individual in need thereof to combat, ameliorate, relieve, reduce, prevent or care for hematologic malignancies. Suitable ROCK inhibitors may be, for example, H-1152, fasudil, dimethyl fasudil, and Y27632.

Therapeutically effective amounts of the ROCK inhibitor H-1152 may be, for example, from about 50 mg/kg body weight to about 100 mg/kg body weight, when orally administered. Thus, suitable dosage amounts may be from about 3 grams to about 7 grams. Therapeutically effective amounts of the ROCK inhibitor fasudil may be, for example, from about 25 mg/kg body weight to about 50 mg/kg body weight, when intraperitoneally administered. Thus, suitable dosage amounts may be from about 1 gram to about 5 grams. Administration of a therapeutically effective amount may be by a single dose, multiple doses, as part of a dosage regimen, and combinations thereof as determined by those skilled in the art for the relevant mechanism or process. The dosage may vary depending on the symptoms, age and body weight of the individual, the nature and severity of the disorder to be treated or prevented, the route of administration and the form of the drug.

Particularly suitable hematologic malignancies for treatment according to the disclosed method may be those associated with an oncogene. Oncogenes associated with hematologic malignancies for treatment according to the disclosed method may be, for example, ROCK, KIT, FLT3, BCR-ABL, MLL-AF9 and MPLW515L. ROCK may be, for example, ROCK1 and ROCK2.

ROCK inhibitors may be administered by any method known to those skilled in the art. Suitable methods for administering the ROCK inhibitor may be, for example, orally, injected (e.g., intravenously, intraperitoneally, intramuscularly, and subcutaneously), drop infusion preparations, ointments, drops, and the like Inhibitors prepared as described herein may be administered in various forms, depending on the disorder to be treated and the age, condition, and body weight of the individual, as is well known in the art.

ROCK inhibitors may be administered as pharmaceutical compositions and pharmaceutically acceptable formulations that include pharmaceutically acceptable carriers. As used herein, the phrase "pharmaceutically acceptable" refers to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the individual.

Pharmaceutically acceptable carriers may be, for example, excipients, vehicles, diluents, and combinations thereof For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent.

In another aspect, the present disclosure is directed to a method of treating hematologic malignancies that includes administering a myosin light chain (MLC)-specific inhibitory RNA molecule or a fragment or derivative thereof As used herein, the terms "inhibitory RNA molecule" and "RNAi molecule" are generic terms referring to double stranded RNA molecules including small interfering RNAs (siRNAs), hairpin RNAs (shRNAs), and other RNA molecules which can be cleaved in vivo to form siRNAs Inhibitory RNA molecules may include either long stretches of dsRNA identical or substantially identical to the target nucleic acid sequence or short stretches of dsRNA identical or substantially identical to only a region of the target nucleic acid sequence. The isolated RNA molecules of the present disclosure mediate degradation of mRNA that is the transcriptional product of the myosin light chain gene. RNA of the present disclosure need only be sufficiently similar to natural RNA that it has the ability to mediate RNAi. As used herein the phrase "mediate RNAi" refers to and indicates the ability to distinguish which mRNA are to be affected by the RNAi machinery or process. RNA that mediates RNAi interacts with the RNAi machinery such that it directs the machinery to degrade particular mRNAs or to otherwise reduce the expression of the target protein. It is not necessary that there be perfect correspondence of the sequences, but the correspondence must be sufficient to enable the RNA to direct RNAi inhibition by cleavage or lack of expression of the target myosin light chain mRNA. Suitable inhibitory RNA molecules may be, for example, shRNAs (hairpin RNAs), siRNAs (small inhibitory RNAs), and other RNA molecules that may be cleaved in vivo to form siRNAs.

The terms "fragment" and "derivative" refer to nucleic acids that may differ from the original nucleic acid in that they are extended or shortened on either the 5' or the 3' end, on both ends or internally, or extended on one end, and shortened on the other end, provided that the function of the resulting RNAi molecule, namely the down-regulation of the target gene, is not abolished or inhibited. The terms "fragment" and "derivative" also refer to nucleic acids that may differ from the original nucleic acid in that one or more nucleotides of the original sequence are substituted by other nucleotides and/or (chemically) modified by methods available to the skilled person, provided that the function of the resulting RNAi molecule is not abolished or inhibited. The "fragment" and "derivative" nucleic acid may typically show at least 80%, e.g., at least 85%, preferably at least 90%, e.g., at least 95% or even at least 99% sequence identity to the original nucleic acid. Sequence identity between two nucleotide sequences can be calculated by aligning the said sequences and determining the number of positions in the alignment at which the two sequences contain the same nucleic acid base vs. the total number of positions in the alignment.

A particularly suitable MLC-specific inhibitory RNA molecule is a MLC-specific shRNA. A particularly suitable MLC-specific shRNA includes SEQ ID NO: 1 (CGCG-CAACCTCCAATGTGTTCGCCATGTT). It shall be clear to a person of skill in the art that any of the above-given sequences or complementary sequences thereof may be used to prepare an RNAi molecule, i.e. a double stranded RNA molecule. Those skilled in the art know how to prepare an RNAi molecule using well known methods.

Particularly suitable hematologic malignancies for treatment by administering the MLC-specific inhibitory RNA molecule are those associated with oncogenes. As used herein, "treatment" refers to the administration or application of a MLC-specific inhibitory RNA molecule to an individual in need thereof to combat, ameliorate, relieve, reduce, prevent or care for hematologic malignancies. Particularly suitable oncogenes may be, for example, ROCK, KIT, FLT3, BCR-ABL, MLL-AF9 and MPLW515L.

Without being bound by theory, administering the MLC-specific inhibitory RNA molecule is believed to knockdown the expression of myosin light chain in cells associated with the hematologic malignancy. This leads to dephosphorylation of myosin light chain, actin filament destabilization and disruption of the actin cytoskeleton leading to cell death.

There are several well-known methods of introducing (ribo)nucleic acids into animal cells, any of which may be used and which may depend on the host. Methods for administering inhibitory RNA molecules may be, for example, by passive uptake, through the use of one or more vectors, transfection, biolistic particle bombardment (e.g., gene gun), attachment to a nanoparticle, encapsulation in a microparticle and/or nanoparticle, lipid-mediated transfection, calcium phosphate transfection, retroviral transfection, and combinations thereof. For example, the nucleic acid may be directly injected into the target cell/target tissue. Other methods may be, for example, fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, infection with viral vectors, electroporation, and the like. Other techniques or methods which are suitable for delivering RNAi molecules to target cells include the continuous delivery of an RNAi molecule from poly(lactic-Co-Glycolic Acid) polymeric microspheres or the direct injection of protected (stabilized) RNAi molecule(s) into micropumps delivering the product in the hole of surgical resection to the tumor cells still present at the site of surgery. Convection-enhanced delivery of stabilized RNAi molecules may also be used. Another possibility is the use of implantable drug-releasing biodegradable microspheres. Combinations of different above-mentioned delivery modes or methods may be used.

Methods of Identifying Drug Candidates

In another aspect, the present disclosure is directed to a method of identifying drug candidates for inhibiting ROCK in hematologic malignancies. The method includes culturing a first cell expressing an oncogene selected from the group consisting of ROCK, KIT, FLT3, BCR-ABL, MLL-AF9 and MPLW515L; culturing a second cell expressing an oncogene selected from the group consisting of ROCK, KIT, FLT3, BCR-ABL, MLL-AF9 and MPLW515L; contacting the drug candidate with the first cell; measuring ROCK activity of the first cell after contacting with the drug candidate; measuring ROCK activity of the second cell, wherein the second cell is not contacted with the drug candidate; and comparing the ROCK activity of the first cell with the ROCK activity of the second cell. A drug candidate may be identified by observing an effect on the first cell that is contacted with the drug candidate. Such an effect may be, for example, cell death, cell survival, an effect on cell proliferation, an effect on cytoskeletal protein staining, an effect on cytoskeletal protein expression, an effect on focal adhesion protein staining, an effect on focal adhesion protein expression, an effect on myosin phosphatase phosphorylation, an effect on myosin light chain expression and combinations thereof These observations may be made using methods known by those skilled in the art. Suitable methods may be, for example, cell counting, immunofluorescence staining, in situ hybridization, thymidine incorporation assay, flow cytometry, Western blot analysis, Northern blot analysis, Southern blot analysis, polymerase chain reaction (PCR), and combinations thereof.

As used herein, the terms "culturing", "culture", and "cultured" are used according to their ordinary meaning as understood by those skilled in the art to refer to growing cells under controlled conditions.

The first cell and the second cell may be obtained from a subject diagnosed with a hematologic malignancy. Thus, the method may involve additional steps to obtain cells from the subject as well as additional steps and methods to remove cells from the subject, isolate cells, and purify cells according to methods known to those skilled in the art.

Alternatively, the first cell and the second cell may be obtained from a cell line derived from a hematologic malignancy.

The first cell and the second cell may also be transformed or transfected with at least one oncogene according to methods described herein and methods known to those skilled in the art such that the cells express the oncogene(s).

The method may further include determining ROCK activity of the first cell after contacting with the drug candidate and determining ROCK activity of the second cell, which is not contacted with the drug candidate. After determining the ROCK activities, they are compared to determine whether the drug candidate affected ROCK activity. If, for example, ROCK activity in the first cell is decreased after being contacted with the drug candidate when compared to the ROCK activity of the second cell, one may conclude that the drug candidate may be a ROCK inhibitor.

The method may further include determining the level of myosin phosphatase phosphorylation, determining cell growth, and/or determining myosin light chain phosphorylation of the first cell after contacting with the drug candidate as compared to the second cell. Determining the levels of myosin light chain phosphorylation and myosin phosphatase phosphorylation may be done by methods disclosed herein and any methods known to those skilled in the art such as, for example, thymidine incorporation and cell counting. Determining the level of growth of the cells may be done by methods disclosed herein and any methods known to those skilled in the art such as, for example, thymidine incorporation and cell counting.

If, for example, the level of myosin phosphatase phosphorylation in the first cell is decreased as compared to the level of myosin phosphatase phosphorylation in the second cell one may conclude that ROCK activity in the first cell is decreased after being contacted with the drug candidate when compared to the ROCK activity of the second cell, and thus, the drug candidate may be a ROCK inhibitor. Similarly, if the level of myosin light chain phosphorylation in the first cell is decreased as compared to the level of myosin light chain phosphorylation in the second cell one may conclude that ROCK activity in the first cell is decreased after being contacted with the drug candidate when compared to the ROCK activity of the second cell, and thus, the drug candidate may be a ROCK inhibitor. If, for example, the growth of the first cell is decreased as compared to the level of myosin phosphatase phosphorylation in the second cell one may conclude that ROCK activity in the first cell is decreased after being contacted with the drug candidate when compared to the ROCK activity of the second cell, and thus, the drug candidate may be a ROCK inhibitor.

The disclosure will be more fully understood upon consideration of the following non-limiting Examples.

EXAMPLES

Experimental Procedures

Antibodies and Reagents

Rabbit anti-phospho-MYPT1 antibody was purchased from Upstate Biotechnology (Lake Placid, N.Y.). Rabbit anti-phospho-AKT, anti-AKT, anti-phospho-ERK, anti-ERK, anti-phospho-Stat5, anti-Stat5, anti-phospho-PKC, mouse anti-phospho-MLC and anti-MLC antibodies were purchased from Cell Signaling Technology (Beverly, Mass.). Rabbit anti-ROCK1 antibody was purchased from Santa Cruz Biotechnology Inc. (Santa Cruz, Calif.). Phycoerythrin (PE)-conjugated annexin V antibody and 7-amino actinomycin D (7-AAD) were purchased from BD Biosciences Pharmingen (San Jose, Calif.). ROCK inhibitors (fasudil and Y-27632) were purchased from Calbiochem (San Diego, Calif.). Imatinib was purchased from Toronto Research Chemicals Inc. (North York, Ontario, Canada). C3 exoenzyme was purchased from Cytoskeleton Inc. (Denver, Colo.). Recombinant murine and human IL-3, FLT3, GM-CSF, SCF, IL-6, and Tpo were purchased from Peprotech (Rocky Hill, N.J.). Retronectin was obtained from Takara (Madison, Wis.). Iscove's modified Dulbecco's medium (IMDM) was purchased from Invitrogen (Carlsbad, Calif.). Monothioglycerol was purchased from Sigma (St. Louis, Mo.). [3H] Thymidine was purchased from PerkinElmer (Boston, Mass.). ROCK inhibitor H-1152 was synthesized as described (U.S. Pat. No. 6,153,600, Nov. 28, 2000). Retroviral expression plasmids of dominant negative mutant of RhoA (RhoAN19) and Imatinib-resistant BCR-ABLT315I mutant were a gift from Dr. Yi Zhang and Dr. Jose Cancelas, respectively, from Cincinnati Children's Hospital Medical Center, Cincinnati.

Mice

C57BL/6 mice and C3H/HeJ mice were purchased from Jackson Laboratory (Bar Harbor, Me.). p85α$^{+/-}$ and ROCK1$^{-/-}$ mice were maintained under specific-pathogen-free conditions at the Indiana University Laboratory Animal Research Center, Indianapolis, Ind. All animal procedures were conducted in accordance with the Guidelines for the Care and Use of Laboratory Animals and were approved by the Institutional Animal Care and Use Committees (IACUCs) at Indiana University School of Medicine.

Patient Samples

Blast cells from the bone marrow of patients with AML were obtained at the time of diagnostic testing. Approval was obtained from the institutional review boards of Indiana University School of Medicine. The buoyant fraction was isolated over Ficoll-Hypaque, and then washed with phosphate-buffered saline (PBS) before processing.

Cells

The murine IL-3 dependent myeloid cell line 32D cells bearing MIEG3 vector, KIT, KITD814V, BCR-ABL, BCR-ABLT315I mutant or RhoAN19 were cultured in medium containing IMDM supplemented with 10% fetal bovine serum (FBS) and murine IL-3 (10 ng/mL). The murine IL-3 dependent and G418 resistant pro-B cell line BaF3 bearing FLT3 and FLT3N51 were cultured in medium containing IMDM supplemented with 10% FBS, G418 (2 mg/mL), and murine IL-3 (5 ng/mL). The Human mast cell leukemia line, bearing the KITV560G as well as KITD816V mutations, HMC1.2 and acute myeloid leukemia (AML) cell line, bearing the FLT3-ITD mutation, MV4-11 were obtained from the American Type Culture Collection (Manassas, Va.) and cultured in medium containing IMDM supplemented with 15% FBS and 1.2 mM monothioglycerol.

Construction of Wild-Type (WT) and Mutant KIT or CHR Oncogenic Receptors

KIT and KITD814V were inserted into the bicistronic retroviral vector, MIEG3, upstream of the internal ribosome entry site (IRES) and the enhanced green fluorescent protein (EGFP) gene. Utilizing Chimeric KIT receptors (CHR) as template, we generated the mutant CHRD814V and CHRD814V with none (CHRD814V-F7) or single intracellular tyrosine add-back mutant at 719 (CHRD814V-Y719) using the Quick change Site-Directed Mutagenesis kit (Stratagene, La Jolla, Calif.) and the following primer pair (SEQ ID NO: 2: forward: 5'-GGGCTAGCCAGAGTCATCAGGAATGATTCG-3; SEQ ID NO: 3: reverse: 5'-CGAATCATTCCTGATGACTCTGGCTAGCCC-3'). All of these mutated CHRD814V receptors were verified by direct sequencing.

Expression of WT and Oncogenic Receptors

Retroviral supernatants for transduction of 32D and primary HSC/Ps were generated using the Phoenix ecotropic packaging cell line transfected with retroviral vector plasmids using a calcium phosphate transfection kit (Invitrogen, Carlsbad, Calif.). Supernatants were collected 48 hours after transfection and filtered through 0.45 μM membranes. 32D cells were infected with 2 mL high-titer virus supernatant in the presence of polybrene (8 μg/mL) and IL-3 (10 ng/mL). Low density mononuclear cells (LDMNCs) were suspended in IMDM containing 20% FBS and 1% penicillin/streptomycin, and pre-stimulated in non-tissue culture plates supplemented with SCF (100 ng/mL), FL T3L (50 ng/mL), IL-6 (4 ng/mL), and Tpo (100 ng/mL) for 48 hours prior to retroviral infection on fibronectin fragments. After infection, 32D and primary HSC/Ps bearing the vector, WT or oncogenic receptors were sorted to homogeneity based on EGFP expression and used to perform all experiments.

shRNA Silencing of Myosin Light Chain (MLC)

The myosin light chain (MLC)-specific shRNA (SEQ ID NO: 1: CGCGCAACCTCCAATGTGTTCGCCATGTT) expression plasmid in retroviral vector pGFP-V-RS was purchased from OriGene Technologies (Rockville, Md.). Purified and sequence verified plasmid containing a non-effective 29-mer sh eGFP cassette (Scrambled vector) was used as a negative control. Cells were transduced with scrambled vector or shRNA plasmid as described above. After infection, cells were grown in the presence of puromycin (10 ng/mL) to select the transduced cells.

Proliferation Assay

Proliferation was assessed by conducting a thymidine incorporation assay. Cells were washed twice with warm IMOM and starved in IMOM containing 0.2% BSA for 6 to 7 hours. Cells (at a density of $5 \times 10^4$) were plated in a 96-well plate in 200 μL complete medium (IMOM containing 10% FBS, 2% Penicillin and Streptomycin) either in the absence or in presence of IL-3 (10 ng/mL) and indicated concentrations of different inhibitors. Cells were cultured for 48 hours and subsequently pulsed with 1.0 μCi (0.037 MBq) [$^3$H] thymidine for 6 to 8 hours. Cells were harvested using an automated 96-well cell harvester (Brandel, Gaithersburg, Md.) and thymidine incorporation was determined as counts per minute (CPM).

Western Blot Analysis

Cells were lysed in lysis buffer and centrifuged at 10,000 rpm for 5 min at 4° C. Supernatants were collected and protein concentration was determined using the BCA protein assay (Thermo Fisher Scientific, Rockford, Ill.). Equal amounts of protein extracts were mixed with gel loading buffer and separated on SDS-polyacrylamide gels. After electrophoresis, the proteins were transferred onto nitrocellulose membranes and nonspecific binding was blocked with 5% nonfat dry milk in Tris-buffered saline containing 0.1% Tween-20 (TBS-T). Membranes were then probed with various antibodies overnight at 4° C. on a rocker. After incubation, membranes were washed with TBS-T and incubated with appropriate horseradish peroxidase (HRP)-conjugated secondary antibodies for 1 hour at room temperature. Finally, the proteins on the membranes were detected using SuperSignal West Dura Luminol/Enhancer solution (Thermo Fisher Scientific, Rockford, Ill.) and exposing the membranes to X-ray film.

Analysis of Cell Death

Cells were washed twice with warm IMOM to remove growth factors (IL-3) and starved in IMOM containing 0.2%

BSA for 6 to 7 hours. 2×10$^5$ cells were plated in 24 well plates in the presence and absence of IL-3 and indicated concentrations of different ROCK inhibitors. Forty eight hours after treatment, cells were washed with PBS and the percentage of cell death was determined by annexin V and 7-AAO staining. Cells were re-suspended in 1× annexin V binding buffer and incubated for 30 min at 4° C. Cells were incubated with 5 μL each of annexin V and 7-AAO for 20 min at room temperature in the dark. After incubation, percentage of apoptotic cells (annexin V and 7-AAO positive) was determined using flow cytometry.

F-Actin Measurement

Cells were starved in serum- and cytokine-free media for 6 hours and cultured in the presence or absence of IL-3 and H-1152 for 12 or 24 hours. After treatment, cells were fixed with 4% paraformaldehyde in PBS for 15 min and washed with PBS. After fixing, cells were quenched with 0.1 M glycine in PBS for 15 min and washed with PBS. Then, cells were permeabilized with 0.2% Triton X-100 (w/v) in PBS for 10 min and washed with PBS followed by blocking non-specific binding sites with 5% rat serum containing 0.2% BSA in PBS. Cells were stained with FITC-conjugated phalloidin for 30 min, washed with 0.2% BSA in PBS, and analyzed by flow cytometry.

Mouse Leukemia Induction and In Vivo Drug Treatment

1×10$^6$ 32D cells bearing KIT or KITD814V in 200 μL PBS were injected into C3H/HeJ mice via tail vein. After 48 hours of transplantation, mice were treated with vehicle (PBS) or H-1152 (66 mg/kg body weight) by oral gavage at 12 hours interval for 14 days. In the second study, mice were treated with vehicle, H-1152 (50 mg/kg body weight, oral gavage) or fasudil (25 mg/kg body weight, intraperitoneal) at 24 hour intervals for 21 days. In a separate study, primary HSC/P cells bearing KITD814V were transplanted into syngenic C57BL/6 mice. After 10 days of transplantation, mice were treated with vehicle, H-1152 (50 mg/kg body weight, oral gavage) or fasudil (25 mg/kg body weight, intraperitoneal) at 24 hour intervals for 21 days. In all studies, mice were closely monitored for MPD and harvested at moribund. Bone marrow, spleen, liver and lungs were fixed in 10% buffered formalin and sections were stained with hematoxylin and eosin for histopathologic analysis.

Mouse Bone Marrow Transplantation

A single intraperitoneal injection of 150 mg/kg of 5-fluorouracil (5-FU) (APP Pharmaceuticals, LLC, Schaumburg, Ill.) was given to 8 to 10 weeks old WT C57BU6, WT FVB or Rock1$^{-/-}$ mice. LDMNCs were collected 72 hours post 5-FU injection from tibias, femurs, and iliac crests and prestimulated in non-tissue culture plates supplemented with SCF (100 ng/mL), FLT3L (50 ng/mL), IL-6 (4 ng/mL), and Tpo (100 ng/mL) for 48 hours prior to transduction with retrovirus encoding KIT or KITD814Von fibronectin fragments. After two rounds of infection, cells were sorted to homogeneity based on EGFP expression. 1×10$^6$ transduced cells and 1×10$^5$ supporting fresh splenocytes from syngenic mice were intravenously injected through tail vein into lethally irradiated (1100 cGY-split dose) recipient mice. Transplanted mice were monitored for MPD development and survival. Mice were harvested at moribund and bone marrow, spleen, thymus and peripheral blood were harvested for flow cytometric analysis. Bone marrow, spleen, lungs and liver were fixed in 10% buffered formalin, sectioned, and stained with hematoxylin and eosin.

Statistical Analysis

All graphical data was evaluated by paired Student t-test and results were considered significantly different with p-value <0.05. All data are represented as mean values±standard deviations (SD). Survival probability of transplanted mice groups was compared using a Kaplan-Meier Survival Analysis in which statistical significance was determined as p-values <0.05 by log rank test.

Example 1

In this Example, the role of ROCK signaling in leukemogenesis mediated by activating mutant tyrosine kinases KITD814V, FLT3N51, and BCR-ABL was determined.

Specifically, 32D cells were starved and ROCK activity was analyzed by assessing the phosphorylation of myosin phosphatase (pMYPT1) in the presence or absence of the highly specific and potent ROCK inhibitor H-1152.

Constitutive activation of ROCK was observed only in oncogene bearing cells, but not in cells bearing the empty vector (MIEG3), KIT or FLT3 (FIG. 1A). H-1152 treatment rapidly inhibited the ROCK activity in oncogene bearing cells (FIG. 1). Constitutive ROCK activity was also observed in primary bone marrow (BM) cells expressing KITD814V, but not those expressing the wild type KIT. Moreover, H-1152 treatment completely inhibited the ROCK activity. Furthermore, H-1152 treatment had no effect on the activation of AKT, ERK, Stat5, and PKC in oncogene bearing cells. These results suggest that oncogenes such as KITD814V, BCR-ABL, and FLT3N51 induced constitutive ROCK activation, which was inhibited by H-1152.

Example 2

In this Example, the growth of KITD814V, FLT3N51, and BCR-ABL expressing cells in the presence of ROCK inhibitors was determined.

Specifically, 32D cells bearing MIEG3 or KIT, or BaF3 cells bearing FLT3 showed minimal thymidine incorporation in the absence of growth factors. IL-3 enhances the growth of these cells. In contrast, cells expressing KITD814V, BCR-ABL or FLT3N51 showed constitutive growth in the absence of growth factors, which was repressed by H-1152 in a dose dependent manner. Treatment of cells bearing MIEG3, KIT or FLT3 with H-1152 in the presence of IL-3 showed minimal suppression in proliferation (FIG. 2A). Other ROCK inhibitors fasudil and Y27632 similarly repressed the growth of cells bearing KITD814V or FLT3N51.

To validate whether the suppression in growth of oncogene bearing cells by ROCK inhibitors observed in 32D cells also occurs in primary hematopoietic stem and progenitor cells (HSC/Ps), primary HSC/Ps from C57BL/6 mice were transduced with FLT3 or FLT3N51 and analyzed for proliferation in the presence or absence of ROCK inhibitors.

While primary HSC/Ps bearing the FLT3 grown in the absence of growth factors demonstrated minimal thymidine incorporation, cells bearing the FLT3N51 demonstrated a significant increase in thymidine incorporation in the absence of cytokine (FIG. 2B). When stimulated with IL-3, FLT3 bearing cells demonstrated a significant increase in growth. When these cells were treated with H-1152, a significant reduction in proliferation was observed in cells bearing FLT3N51 but not those expressing FLT3. Consistent with these results, treatment of these cells with less potent ROCK inhibitors fasudil and Y27632 also resulted in significant reduction in the growth of cells expressing FLT3N51, but not cells expressing FLT3 (FIG. 2B). Similar repression in the constitutive growth of primary HSC/Ps was observed in cells bearing KITD814V and BCR-ABL in the presence of ROCK inhibitors.

To determine whether the ROCK pathway is also involved in the constitutive growth of cells bearing the imatinib-resistant BCR-ABLT315I mutant, 32D cells expressing this mutant were treated with H-1152.

Figure 2C:
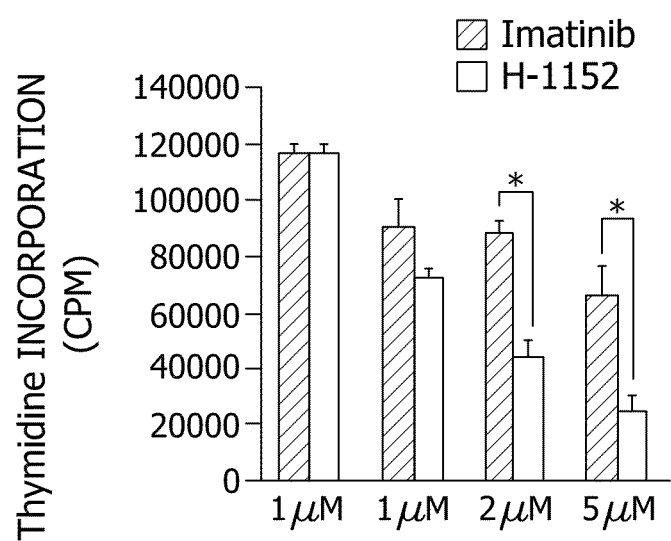
FIG. 2C is a graph showing thymidine incorporation in cells expressing the imatinib-resistant BCR-ABLT315I mutant and treated with imatinib and H-1152 as described in Example 2.

Results demonstrated that imatinib treatment had a minimal effect on the growth of cells bearing BCR-ABLT315I. In contrast, treatment of these cells with H-1152 demonstrated dose dependent suppression in growth (FIG. 2C). These results suggest that ROCK may play a prominent role in supporting the growth of oncogene bearing cells, but only a modest role in supporting the growth of non-oncogene bearing hematopoietic cells.

Example 3

In this Example, the growth of primary bone marrow derived blast cells from AML patients in the presence of ROCK inhibitors was determined.

Figure 3A:
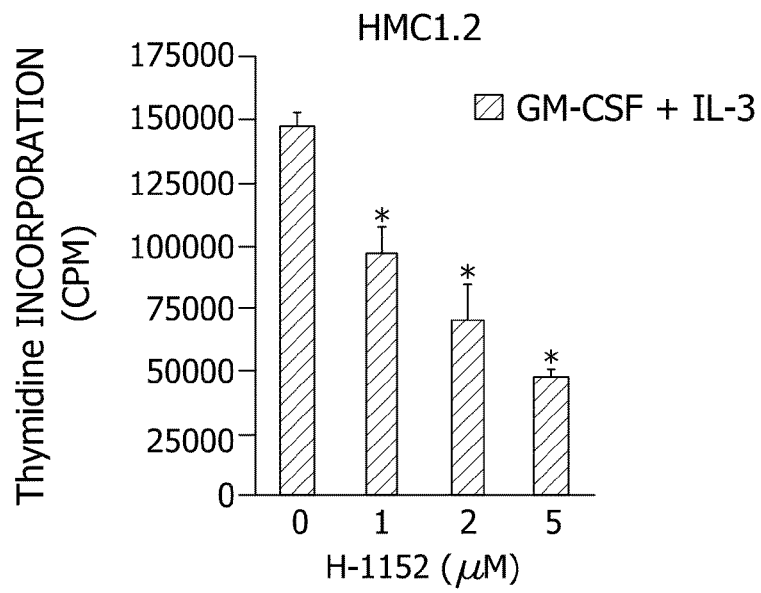
FIG. 3A is a graph showing the dose dependent reduction in growth of HMC1.2 cells expressing the KITV560G mutation treated with H-1152 as described in Example 3.
Figure 3B:
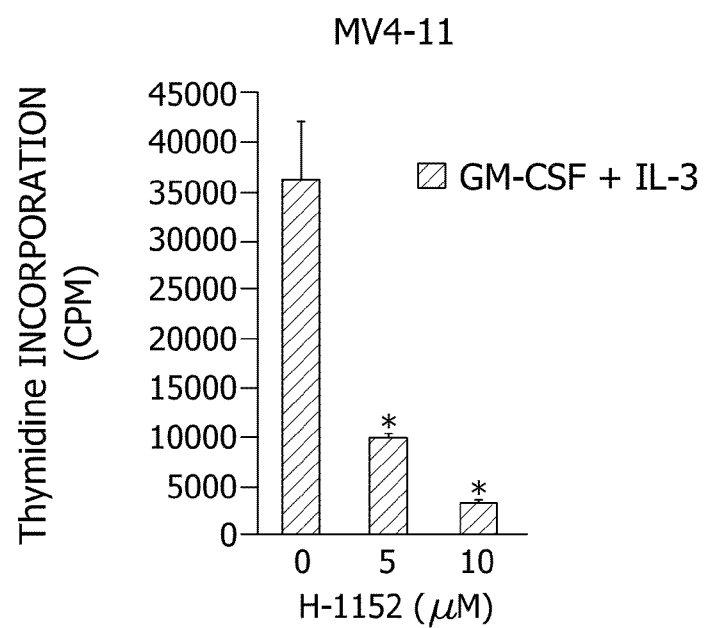
FIG. 3B is a graph showing the dose dependent reduction in growth of MV4-11 cells expressing the FLT3-ITD mutation treated with H-1152 as described in Example 3.
Figure 3C:
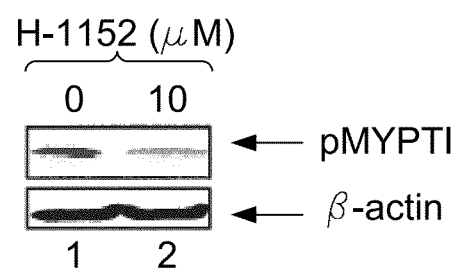
FIG. 3C is a Western blot assessing the phosphorylation of myosin phosphatase (pMYPT1) by ROCK in the presence or absence of H-1152 as described in Example 3.
Figure 3D:
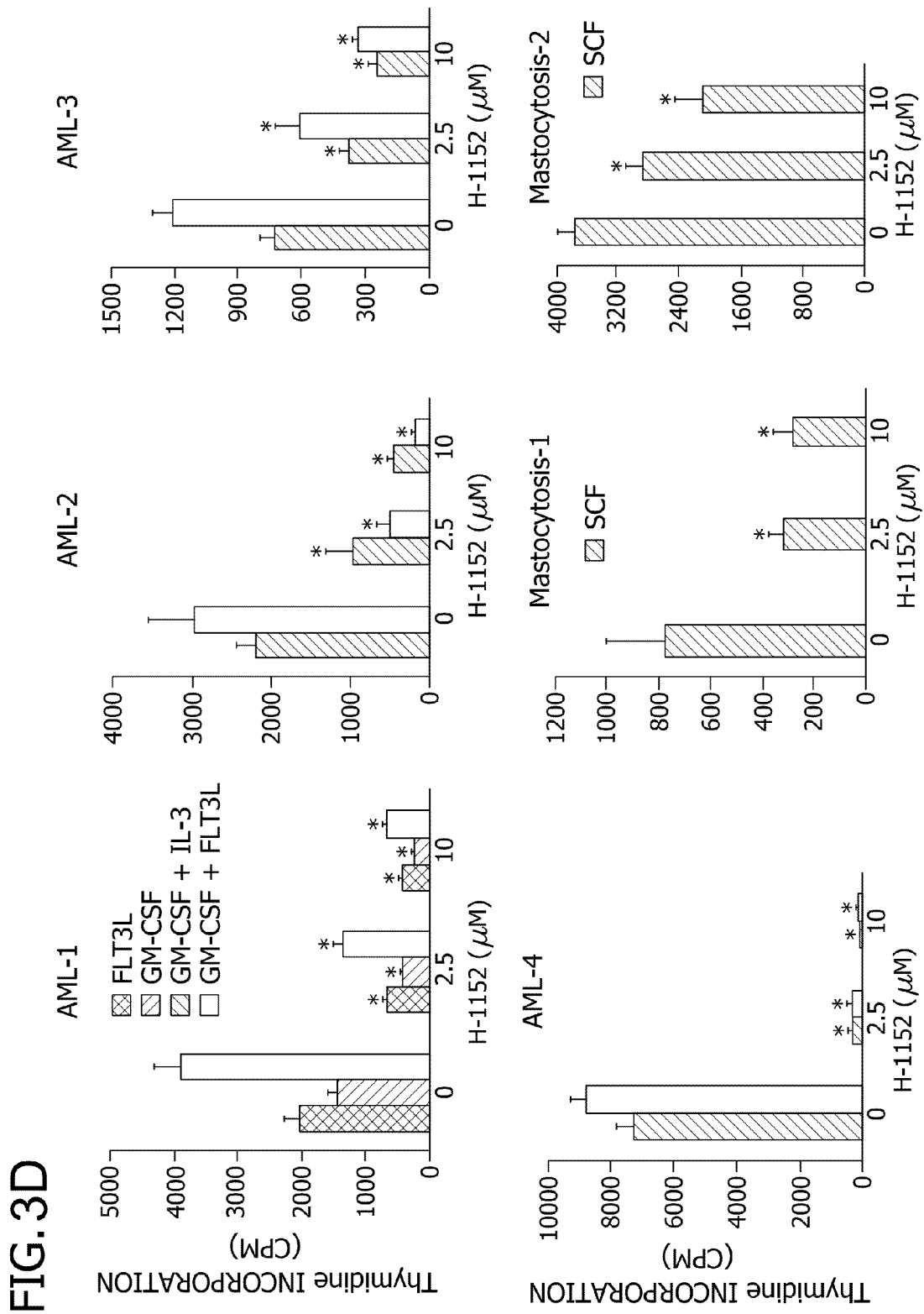
FIG. 3D are graphs showing thymidine incorporation in cells derived from AML and mastocytosis patients and treated with H-1152 as described in Example 3.

Specifically, the growth of HMC1.2 cells bearing the activating KIT mutation (KITV560G and KITD816V) and MV4-11 cells bearing the activating FLT3 mutation (FLT3-ITD) treated with H-1152 was determined. In both instances, H-1152 showed a dose dependent reduction in growth of HMC1.2 and MV4-11 cells (FIGS. 3A and 3B). Likewise, cells derived from AML and mastocytosis patients also demonstrated repression in ROCK activity and growth in the presence of H-1152 (FIGS. 3C and 3D).

Example 4

In this Example, the mechanism of activation of ROCK in oncogene bearing cells was determined.

Figure 4A:
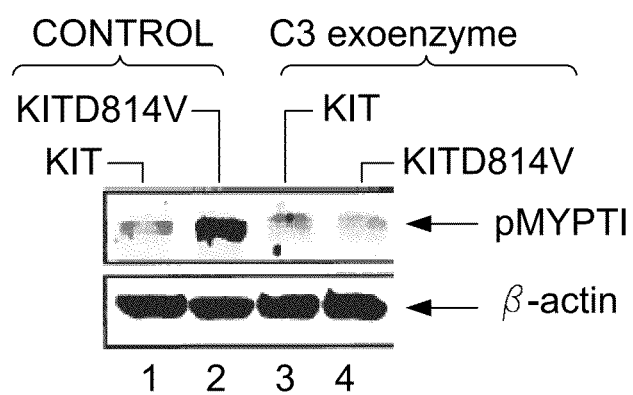
FIG. 4A is a Western blot assessing the phosphorylation of myosin phosphatase (pMYPT1) by ROCK in the presence or absence of C3 exoenzyme as described in Example 4.
Figure 4B:
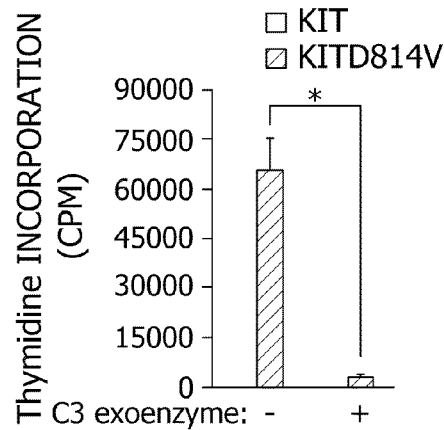
FIG. 4B is a graph showing thymidine incorporation in cells expressing KIT and KITD814V in the presence or absence of C3 exoenzyme as described in Example 4.
Figure 4C:
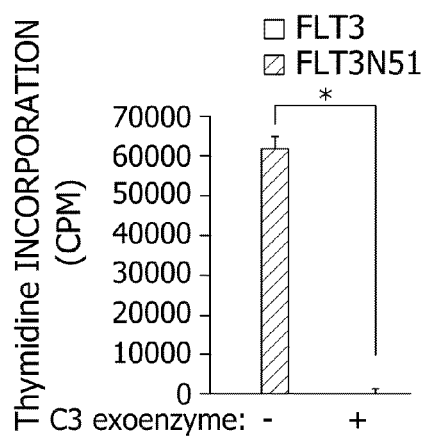
FIG. 4C is a graph showing thymidine incorporation in cells expressing FLT3 and FLT3N51 in the presence or absence of C3 exoenzyme as described in Example 4.
Figure 4D:
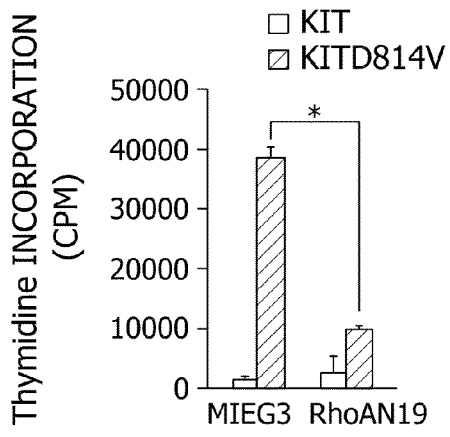
FIG. 4D is a graph showing thymidine incorporation in cells co-infected with KITD814V and a dominant negative RhoA mutant (RhoAN19) or cells co-infected with KITD814V and MIEG3 as described in Example 4.

Specifically, whether the small Rho GTPase, which is upstream of ROCK, is involved in KITD814V induced growth and ROCK activation was determined. C3 exoenzyme (a Rho inhibitor) inhibited the activation of ROCK and the growth of cells bearing KITD814V or FLT3N51 (FIG. 4A-C). In addition, cells co-infected with KITD814V and a dominant negative mutant of RhoA (RhoAN19) showed significantly reduced growth compared to cells expressing KITD814V and MIEG3 (FIG. 4D).

Figure 4E:
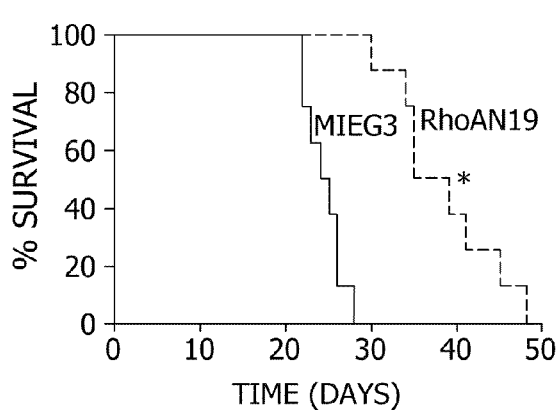
FIG. 4E is a graph showing percent survival of mice transplanted with cells expressing KITD814V and RhoAN19 and mice transplanted with cells expressing KITD814V and MIEG3 as described in Example 4.

Consistent with in vitro findings, mice transplanted with cells bearing KITD814V and RhoAN19 showed significantly prolonged survival compared to cells bearing KITD814V and MIEG3 (FIG. 4E). These results suggest that RhoA is involved in KITD814V induced constitutive growth in vitro and MPD in vivo in part by regulating the activation of ROCK.

Example 5

In this Example, whether PI3K induced MPD of KITD814V bearing cells involves ROCK was determined.

Figure 5A:
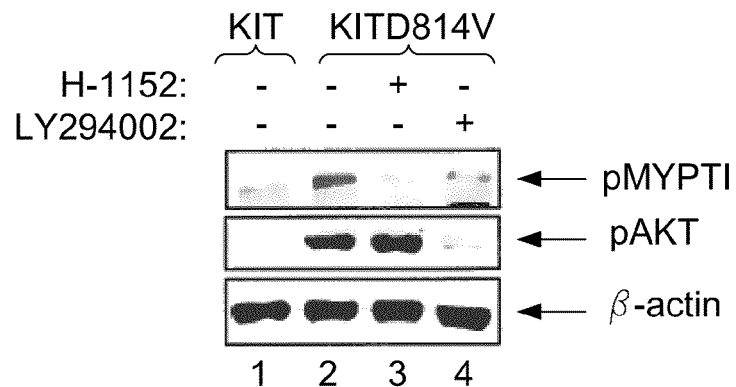
FIG. 5A is a Western blot assessing the phosphorylation of myosin phosphatase (pMYPT1) by ROCK and pAKT by PI3K in the presence or absence of H-1152 and LY294002 as described in Examples 5 and 8.

Specifically, after starved of serum and cytokine for 6 hours, PI3K and ROCK activities were observed only in KITD814V bearing cells, but not in KIT expressing cells (FIG. 5A). Treatment of these cells with H-1152 for 1 hour completely inhibited the activation of ROCK, but had no effect on the activation of AKT. In contrast, one hour treatment with PI3K inhibitor LY294002 completely inhibited the activity of AKT and significantly reduced the activity of ROCK in KITD814V bearing cells. These results suggest that PI3K is important for the activation of ROCK downstream from KITD814V.

Figure 5B:
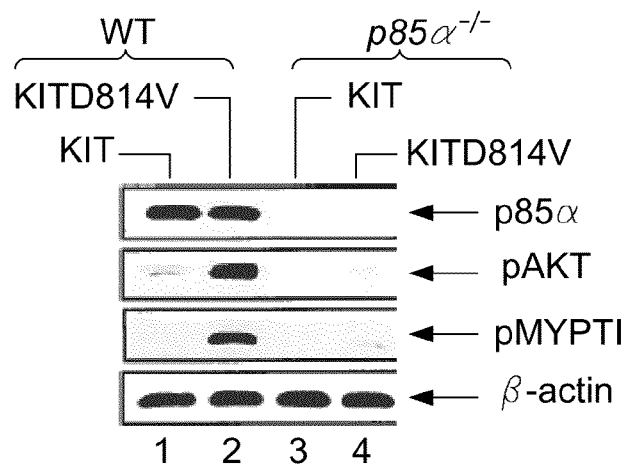
FIG. 5B is a Western blot assessing the phosphorylation of myosin phosphatase (pMYPT1) by ROCK and pAKT by PI3K in primary BM cells transduced from $p85\alpha^{-/-}$ as described in Example 5.

To further analyze the role of PI3K in ROCK activation, primary BM cells from WT and p85α$^{-/-}$ mice transduced with KIT or KITD814V were starved for 6 hours in serum- and cytokine-free medium and the activities of AKT and ROCK were measured. Constitutive activation of PI3K and ROCK was observed in WT cells transduced with KITD814V but not KIT (FIG. 5B). Deletion of p85α resulted in significant inhibition of both AKT and ROCK activity in KITD814V bearing cells. These results provide further support that PI3K is required for the activation of ROCK in KITD814V bearing cells.

To further study the contribution of p85α in ROCK induced MPD, a chimeric KIT receptor CHRKIT and three derivatives CHRD814V, CHRD814V-F7, and CHRD814V-Y719 were generated. CHRD814V corresponds to KITD814V. CHRD814V-F7 has all seven tyrosine residues corresponding to those in KITD814V known to bind SH2 containing proteins (tyrosines 567, 569, 702, 719, 728, 745, and 934) mutated to phenylalanine. CHRD814V-Y719 is similar to CHRD814V-F7 except that tyrosine residue 719 (the binding site for p85α) is preserved.

Figure 5C:
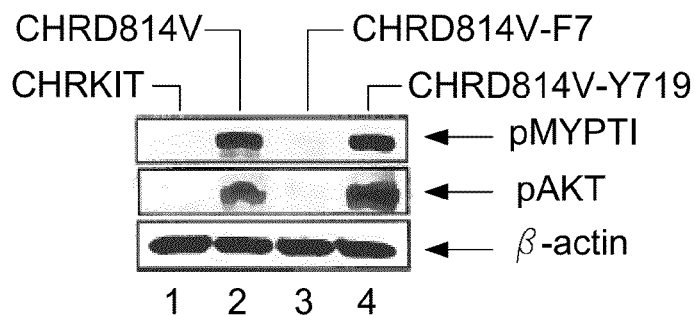
FIG. 5C is a Western blot assessing the phosphorylation of myosin phosphatase (pMYPT1) by ROCK and pAKT by PI3K in cells expressing chimeric KIT (CHRKIT) and three derivatives (CHRD814V, CHRD814V-F7, and CHRD814V-Y719) as described in Example 5.
Figure 5D:
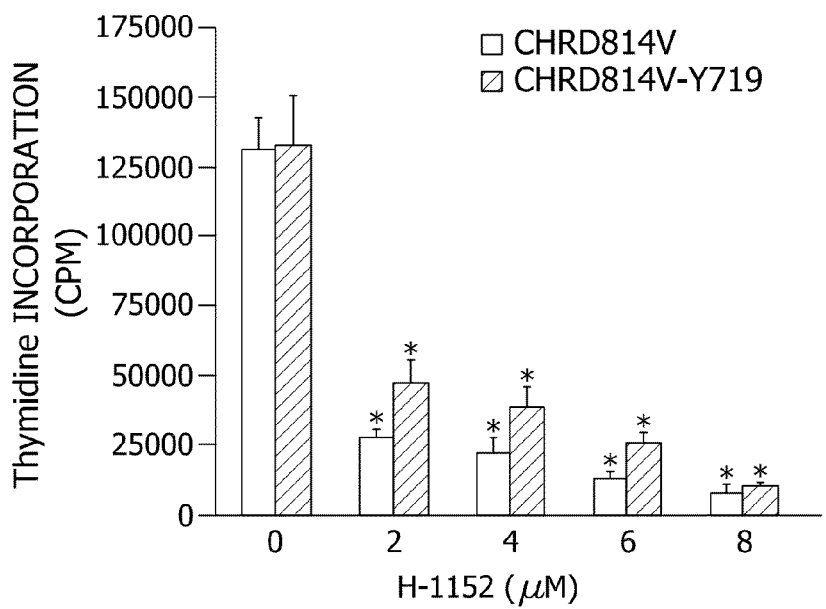
FIG. 5D is a graph showing thymidine incorporation by cells expressing chimeric KIT (CHRKIT) and derivatives (CHRD814V and CHRD814V-Y719) as described in Example 5.
Figure 5E:
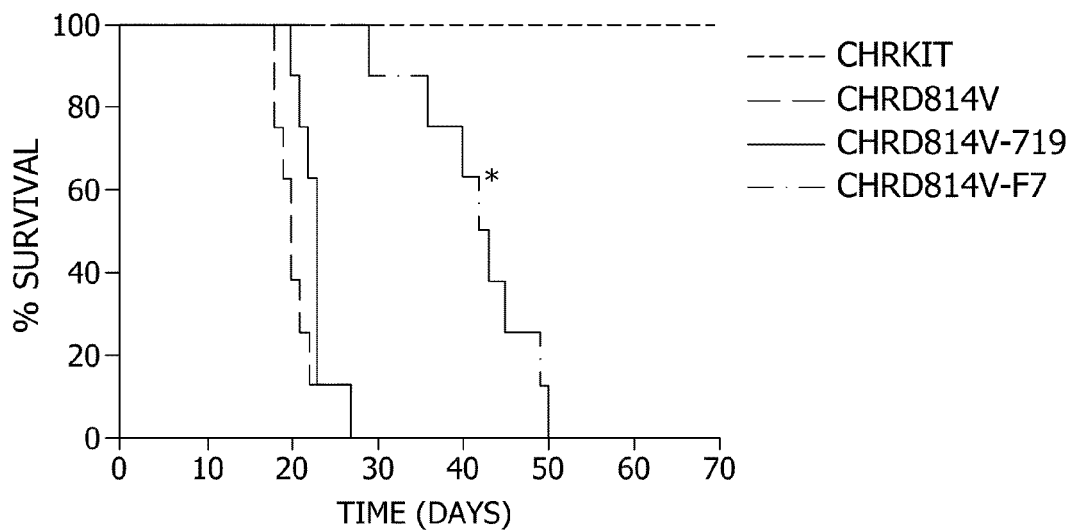
FIG. 5E is a graph showing percent survival of mice transplanted with cells expressing chimeric KIT (CHRKIT) and three derivatives (CHRD814V, CHRD814V-F7, and CHRD814V-Y719) as described in Example 5.

Loss of all tyrosine residues in KITD814V resulted in complete loss of its ability to activate PI3K and ROCK (FIG. 5C). Restoration of the p85α binding site alone in KITD814V was sufficient to completely restore the activation of both AKT and ROCK. Furthermore, cells bearing CHRD814V or CHRD814V-Y719 showed similar levels of ligand independent growth, compared to cells expressing CHRKIT (FIG. 5D). Treatment of cells bearing CHRD814V or CHRD814V-Y719 with H-1152 demonstrated a dose dependent inhibition in constitutive growth (FIG. 5D). In contrast, lack of all tyrosine residues in KITD814V, which cannot activate PI3K or ROCK, resulted in complete suppression of ligand independent growth. Consistent with cells bearing CHRKIT, H-1152 treatment showed only a moderate suppression in growth of cells bearing CHRD814V-F7 in the presence of IL-3 (data not shown). Consistent with in vitro findings, mice transplanted with cells bearing CHRD814V or CHRD814-Y719 succumbed to MPD and died relatively early (within three and a half weeks) after transplantation (FIG. 5E). In contrast, mice transplanted with cells bearing CHRD814V-F7 survived for a significantly longer time and most mice died after 6 to 7 weeks of transplantation. These results demonstrated that p85α mediated activation of PI3K is vital for constitutive activation of ROCK and growth of KITD814V bearing cells in vitro and transformation in vivo.

Example 6

In this Example, the in vivo impact of ROCK inhibitor treatment on KITD814V induced MPD was determined.

Figure 6A:
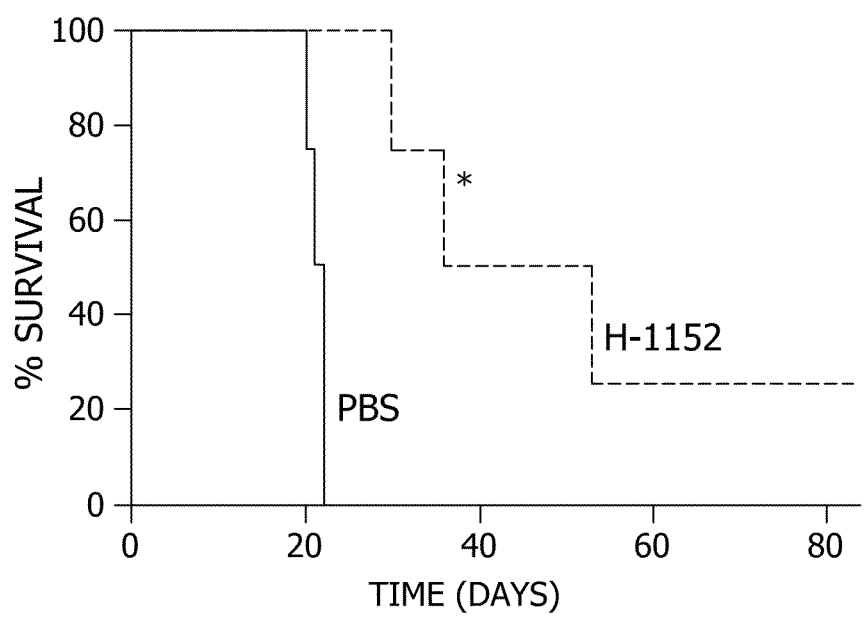
FIG. 6A is a graph showing percent survival of mice transplanted with cells expressing KITD814V and administered H-1152 as described in Example 6.
Figure 6B:
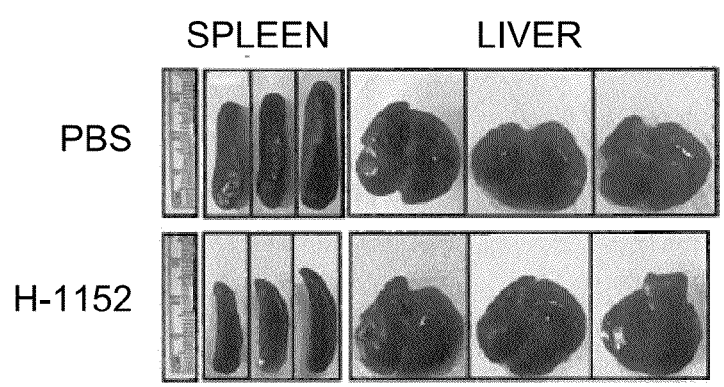
FIG. 6B are photographs showing spleens and livers from mice transplanted with cells expressing KITD814V and administered H-1152 as described in Example 6.
Figure 6C:
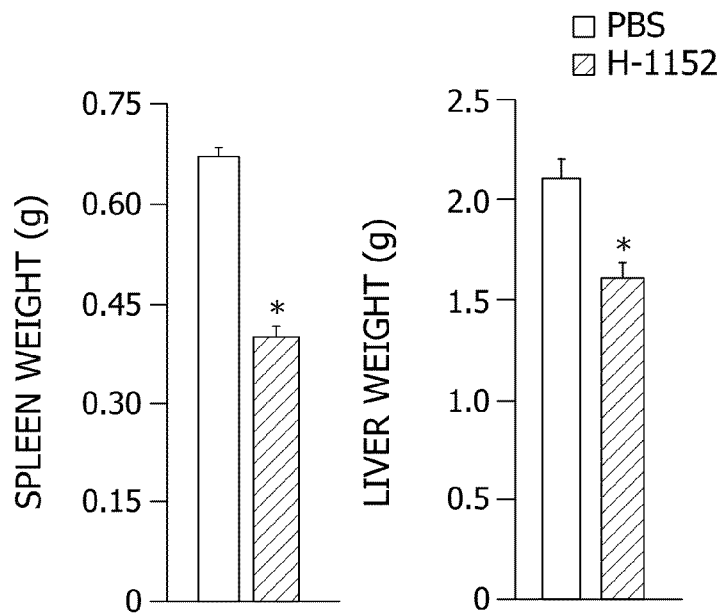
FIG. 6C are graphs showing spleen and liver weights from mice transplanted with cells expressing KITD814V and administered H-1152 as described in Example 6.

Specifically, mice transplanted with cells bearing KITD814V were treated with PBS or H-1152 at 24 hour intervals via oral gavage for 21 days and monitored for MPD and survival. While mice treated with PBS died within 21 days of transplantation, mice treated with H-1152 showed significantly prolonged survival (FIG. 6A). Mice treated with H-1152 showed significantly reduced spleen and liver weight compared to PBS treated mice (FIGS. 6B and 6C).

Figure 6D:
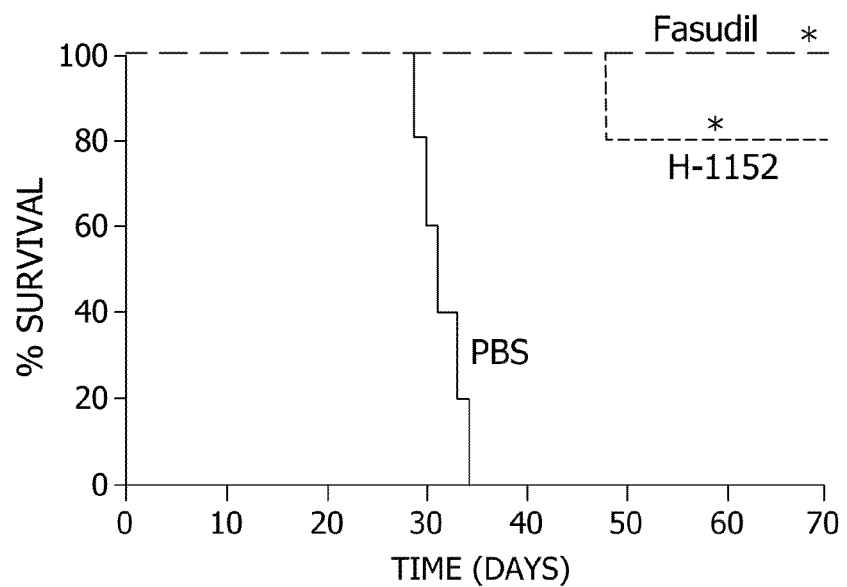
FIG. 6D is a graph showing percent survival of mice transplanted with cells expressing FLT3N51 and administered H-1152 or fasudil as described in Example 6.
Figure 6E:
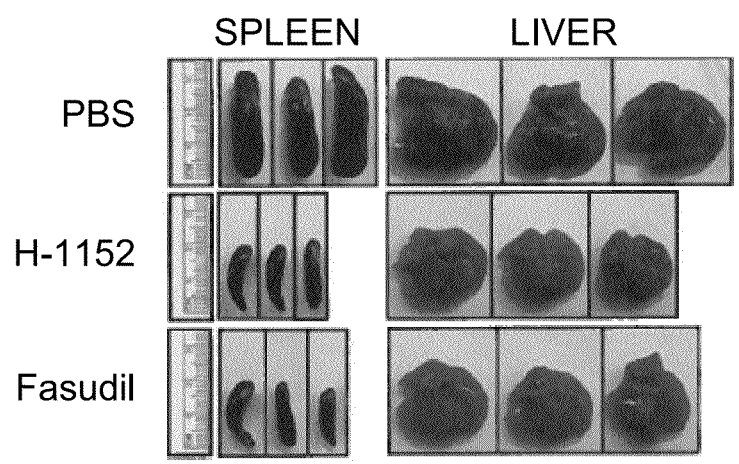
FIG. 6E are photographs showing spleens and livers from mice transplanted with cells expressing FLT3N51 and administered H-1152 or fasudil as described in Example 6.
Figure 6F:
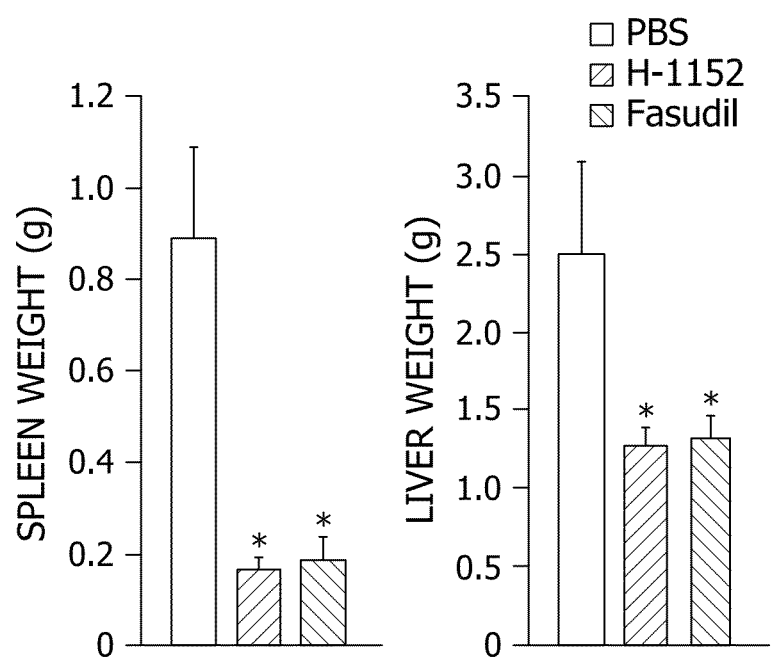
FIG. 6F are graphs showing spleen and liver weights from mice transplanted with cells expressing FLT3N51 and administered H-1152 or fasudil as described in Example 6.

To further determine the efficacy of ROCK inhibitors in treating MPD due to activating mutations in receptor tyrosine kinases, similar pharmacological studies were performed using a different oncogene and a distinct ROCK inhibitor. 32D cells bearing FLT3N51 were transplanted into syngenic C3H/HeJ mice through tail vein. After two weeks of transplantation, mice were treated with PBS (vehicle), H-1152, or fasudil for 21 days and monitored for MPD and survival. While mice treated with PBS died within 34 days of transplantation, treatment with H-1152 significantly prolonged the survival of mice (FIG. 6D). Treatment with fasudil also showed similar efficacy in enhancing the survival of mice bearing FLT3N51 (FIG. 6D). After 5 weeks of prolonged survival compared to PBS treated mice, H-1152 or fasudil treated mice were sacrificed and further analysis were performed. Mice treated with H-1152 or fasudil showed significantly reduced spleen and liver weights compared to PBS treated mice (FIGS. 6E and 6F).

Figure 7A:
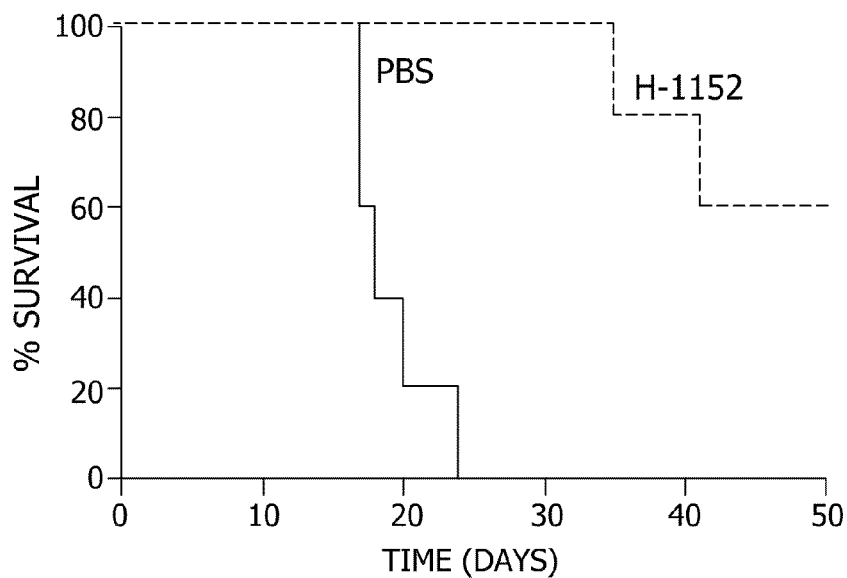
FIG. 7A is a graph showing percent survival of mice transplanted with cells expressing KITD814V and administered H-1152 as described in Example 6.
Figure 7B:
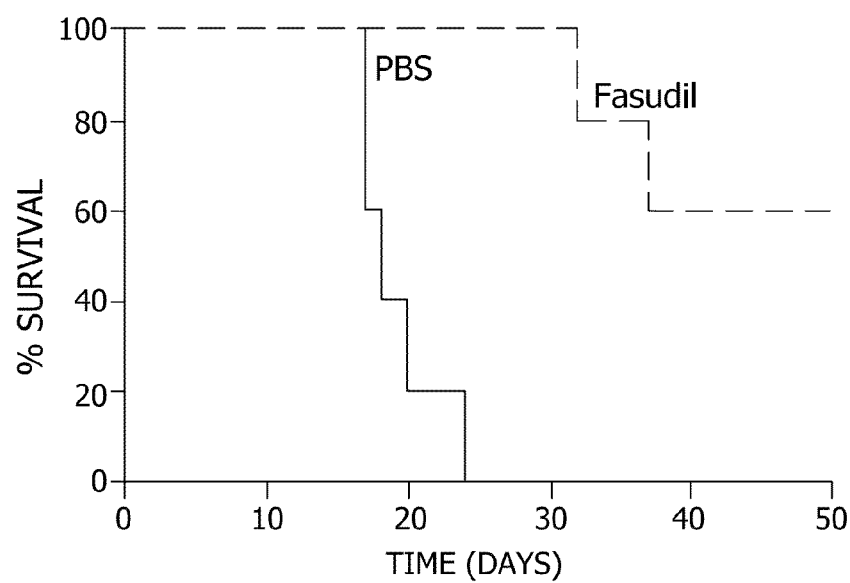
FIG. 7B is a graph showing percent survival of mice transplanted with cells expressing KITD814V and administered fasudil as described in Example 6.
Figure 7C:
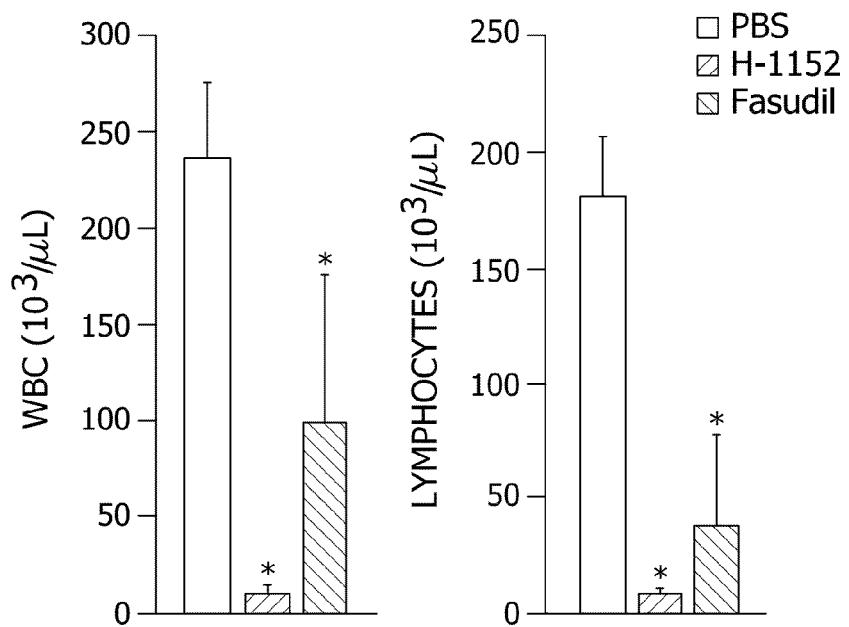
FIG. 7C is a graph showing white blood cell (WBC) and lymphocyte count in mice transplanted with cells expressing KITD814V and administered H-1152 or fasudil as described in Example 6.
Figure 7D:
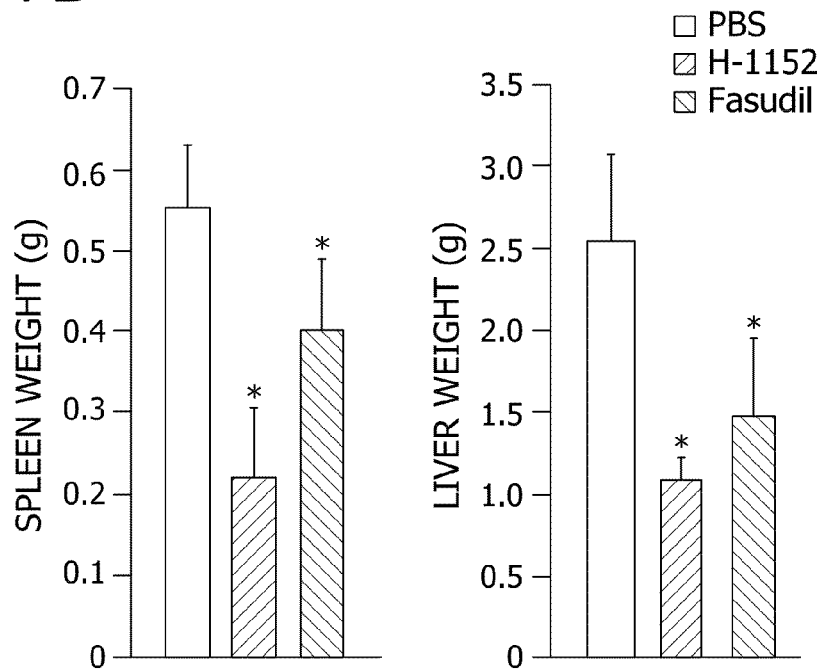
FIG. 7D are graphs showing spleen and liver weights from mice transplanted with cells expressing KITD814V and administered H-1152 or fasudil as described in Example 6.
Figure 7E:
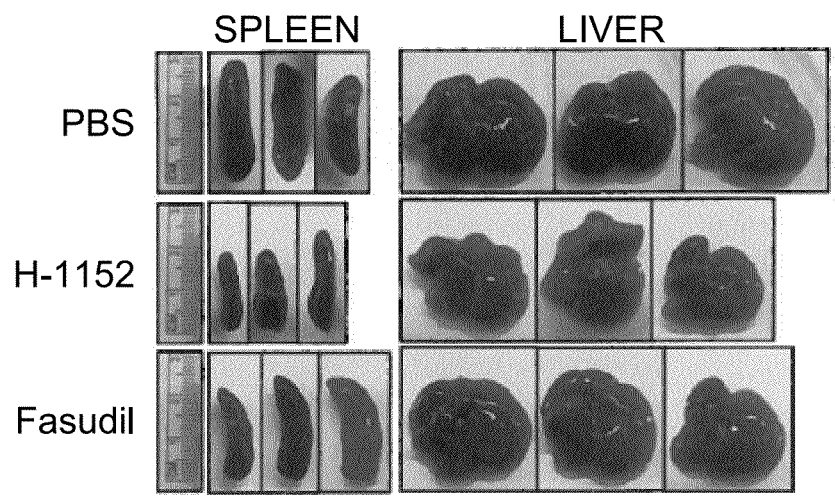
FIG. 7E are photographs showing spleens and livers from mice transplanted with cells expressing KITD814V and administered H-1152 or fasudil as described in Example 6.
Figure 7F:
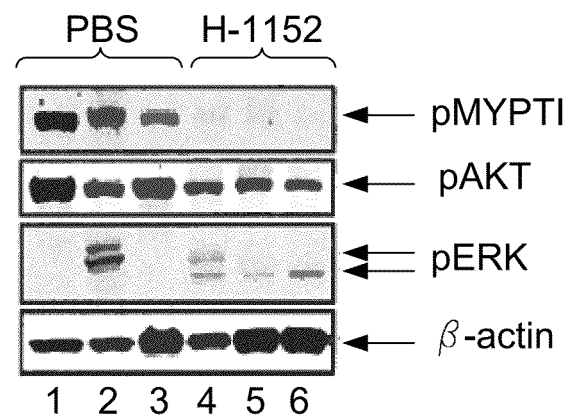
FIG. 7F is a Western blot assessing the phosphorylation of myosin phosphatase (pMYPT1) by ROCK, pAKT by PI3K, and pERK from mice transplanted with cells expressing KITD814V and administered H-1152 as described in Example 6.

To further evaluate the anti-leukemic activity of ROCK inhibitors, additional studies were performed using primary HSC/Ps bearing KITD814V. After 10 days of transplantation, mice were treated with PBS, H-1152, or fasudil for 21 days and monitored for MPD and survival. While PBS treated mice died within 24 days of transplantation, mice treated with H-1152 or fasudil survived significantly longer (FIGS. 7A and 7B). Only 2 out of 5 mice treated with either H-1152 or fasudil died within 37 days of transplantation and the remaining 3 surviving mice were harvested at day 49 post transplant for further analysis. Consistent with the studies with 32D cells, treatment with H-1152 or fasudil significantly modulated the pathological features associated with MPD such as increased white blood and lymphocyte counts as wells as splenomegaly and hepatomegaly (FIGS. 7C and 7F). These results suggest that ROCK inhibitors significantly modulate MPD development in mice transplanted with KITD814V or FLT3N51 bearing cells and prolong the survival of these mice.

Example 7

In this Example, to genetically validate the pharmacologic findings using H-1152, primary HSC/Ps from WT and ROCK1$^{-/-}$ mice were transduced with KIT or KITD814V and proliferation was analyzed.

Figure 8A:
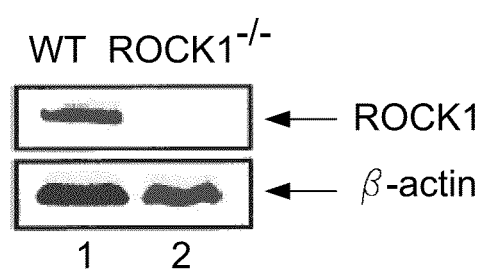
FIG. 8A is a Western blot showing deletion of ROCK1 in $ROCK1^{-/-}$ HSC/Ps as described in Example 7.
Figure 8B:
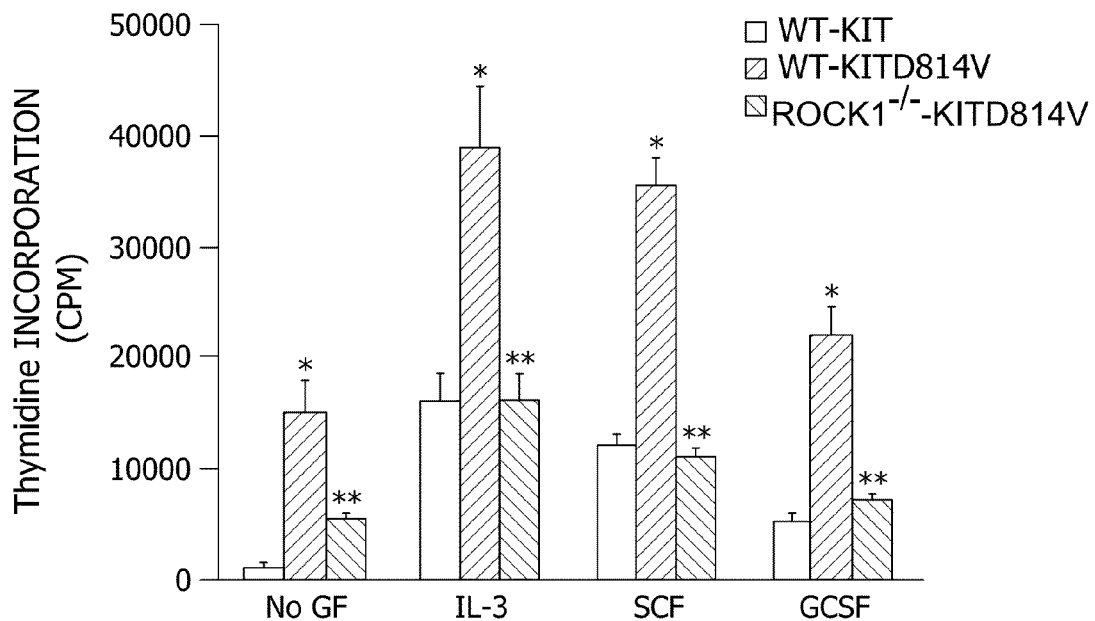
FIG. 8B is a graph showing thymidine incorporation in WT cells transduced with KIT, KITD814V, and ROCK1$^{-/-}$ HSC/Ps expressing KITD814V (ROCK1$^{-/-}$-KITD814V) and grown in the presence of growth factors (IL-3, SCF, and GCSF) as described in Example 7.

FIG. 8A shows deletion of ROCK1 in ROCK1$^{-/-}$ HSC/Ps. Wildtype (WT) cells transduced with KITD814V, but not KIT, showed constitutive growth in the absence of growth factors (FIG. 8B). Hyperproliferation was observed in WT cells transduced with KITD814V compared to KIT in the presence of IL-3, SCF and G-CSF. In contrast, deficiency of Rock1 resulted in correction in the growth of cells bearing KITD814V compared to WT cells in the presence or absence of IL-3, SCF, and G-CSF. In addition, treatment of ROCK1$^{-/-}$ cells bearing KITD814V with H-1152 showed no significant suppression in growth. These results suggest that Rock1 may function as the predominant isoform of ROCK in regulating KITD814V induced growth and MPD.

Figure 8C:
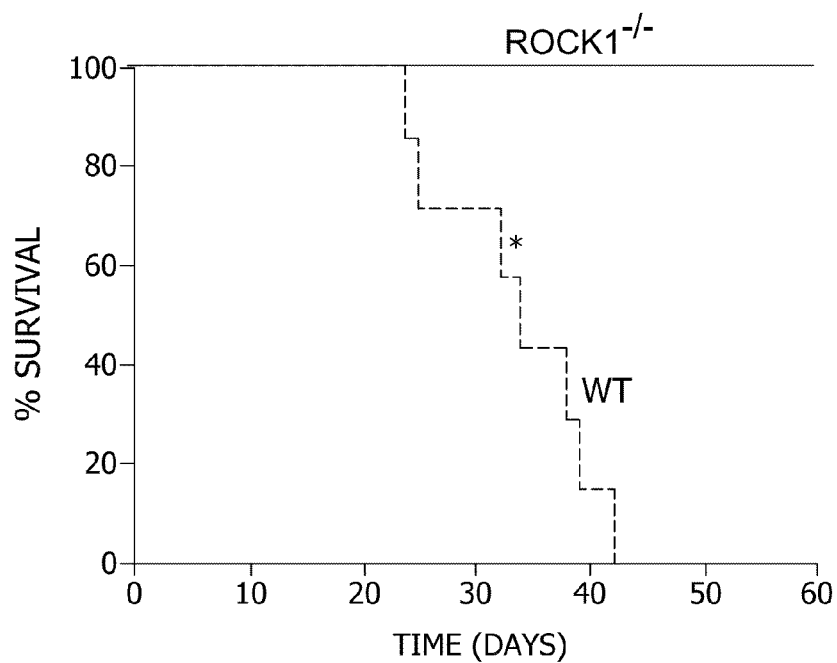
FIG. 8C is a graph showing percent survival of mice transplanted with WT cells expressing KITD814V and ROCK1$^{-/-}$ HSC/Ps expressing KITD814V as described in Example 7.
Figure 8D:
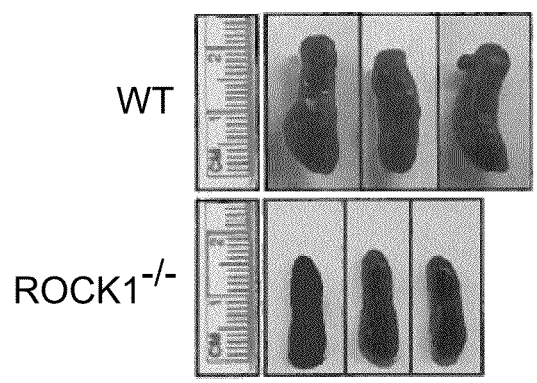
FIG. 8D are photographs showing spleens from mice transplanted with WT cells expressing KITD814V and ROCK1$^{-/-}$ HSC/Ps expressing KITD814V as described in Example 7.
Figure 8E:
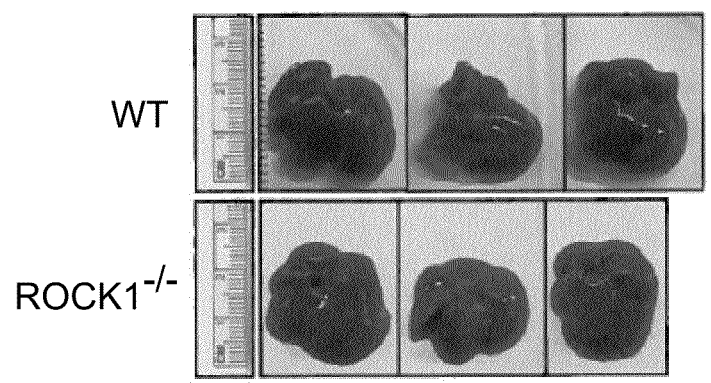
FIG. 8E are photographs showing livers from mice transplanted with WT cells expressing KITD814V and ROCK1$^{-/-}$ HSC/Ps expressing KITD814V as described in Example 7.
Figure 8F:
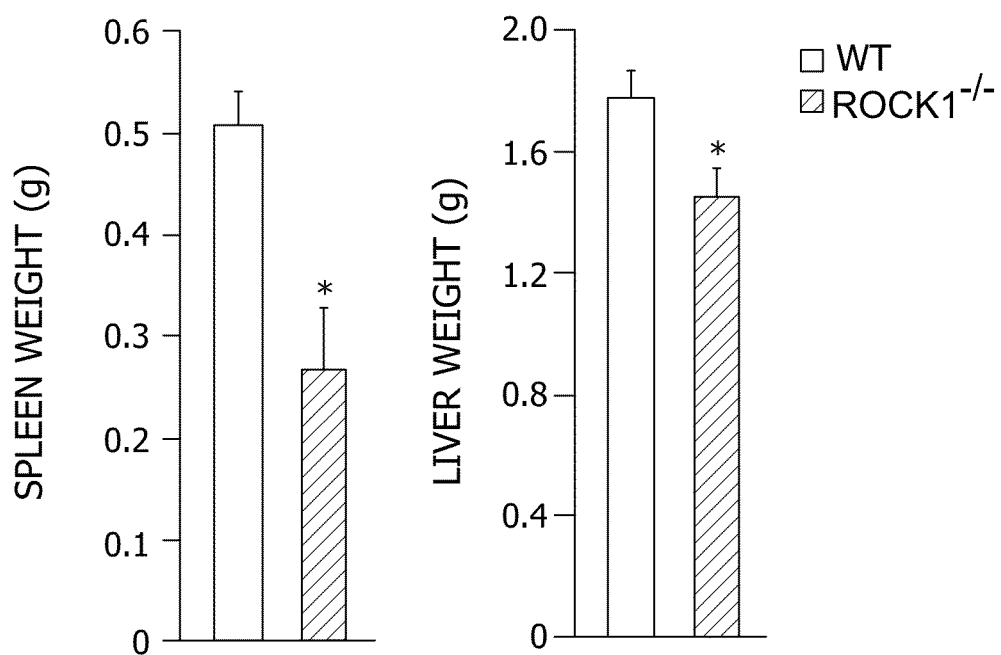
FIG. 8F are graphs showing spleen and liver weights from mice transplanted with WT cells expressing KITD814V and ROCK1$^{-/-}$ HSC/Ps expressing KITD814V as described in Example 7.

To further determine the contribution of ROCK1 in KITD814V induced MPD in vivo, primary HSC/Ps from 5-FU-treated WT or ROCK1$^{-/-}$ mice were transduced with KITD814V and transplanted into recipient mice and monitored for MPD and survival. While all recipient mice transplanted with WT cells bearing KITD814V died within 42 days of transplantation, all recipient mice transplanted with Rock1$^{-/-}$ cells bearing KITD814V survived for the entire duration of the experiment (FIG. 8C). 63 days post transplantation mice expressing KITD814V in ROCK1$^{-/-}$ BM were harvested for further analysis. Mice transplanted with Rock1$^{-/-}$ cells bearing KITD814V showed reduced spleen and liver weights as well as white blood counts compared to mice transplanted with WT cells bearing KITD814V (FIGS. 8D-8F). Furthermore, mice bearing an activating version of ROCK1 also resulted in MPD and hypersensitivity to cytokines.

Example 8

In this Example, the survival of oncogene bearing cells in the presence or absence of ROCK inhibitors was evaluated to determine how ROCK inhibitors might inhibit the growth of oncogene bearing cells.

While H-1152 treatment induced only 5-10% cell death in KIT or MIEG3 bearing 32D cells, treatment of 32D cells bearing the KITD814V or BCR-ABL with H-1152 resulted in significantly greater and a dose dependent increase in cell death. Similar results were observed using BaF3 cells bearing FLT3N51 and Y27632. These results suggest that the reduced growth observed in cells bearing the oncogenes treated with ROCK inhibitors may in part be due to enhanced cell death. Furthermore, ROCK inhibitors are possibly more selective inducers of cell death in oncogene bearing cells relative to WT receptor bearing cells.

Figure 9A:
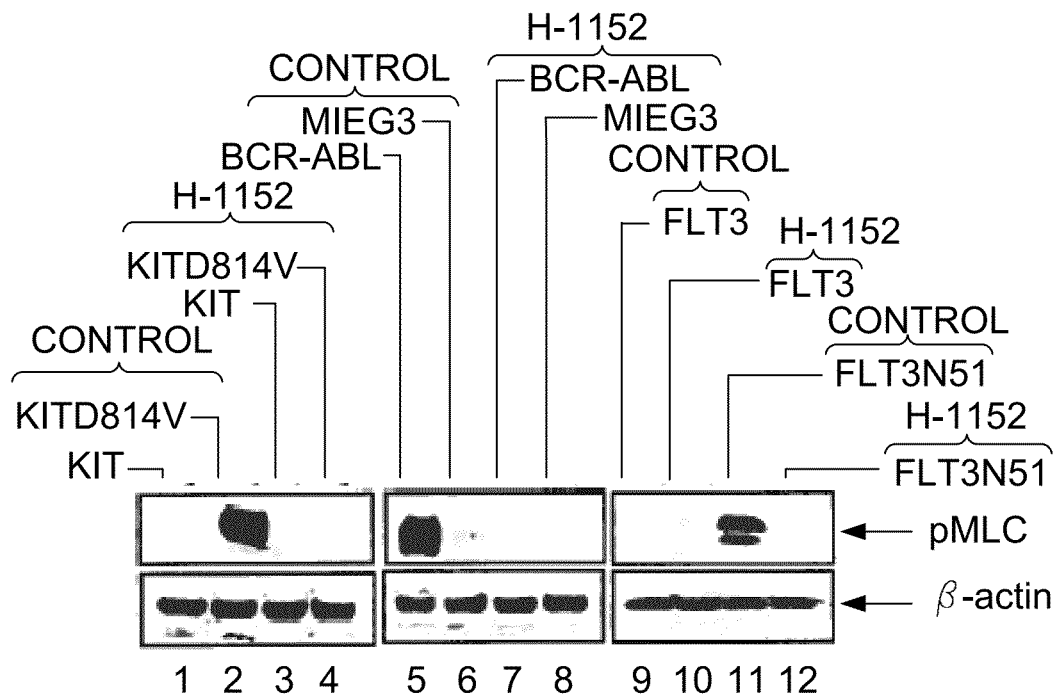
FIG. 9A is a Western blot assessing phosphorylation of myosin light chain (pMLC) in cells expressing KIT, KITD814V, BCR-ABL, MIEG3, FLT3 and FLT3N51 and treated with H-1152 as described in Example 8.

To determine the mechanism(s) by which suppression of ROCK activity induces cell death in oncogene bearing cells, the activation of ERK, AKT, Stat5, PKA and PKC in H-1152 treated cells was investigated. Activation of all of these molecules in oncogene bearing cells was relatively unperturbed in the presence of H-1152 (FIG. 4A and data not shown). While cells bearing KIT, MIEG3 or FLT3 did not show constitutive phosphorylation of MLC, in contrast, cells bearing the KITD814V, BCR-ABL or FLT3N51 demonstrated constitutive phosphorylation of MLC (FIG. 9A). H-1152 completely inhibited the constitutive phosphorylation of MLC within an hour of treatment. These results suggest that constitutive activation of ROCK and phosphorylation of MLC, which is inhibited by H-1152, may contribute to the growth and survival of oncogene bearing cells.

Figure 9B:
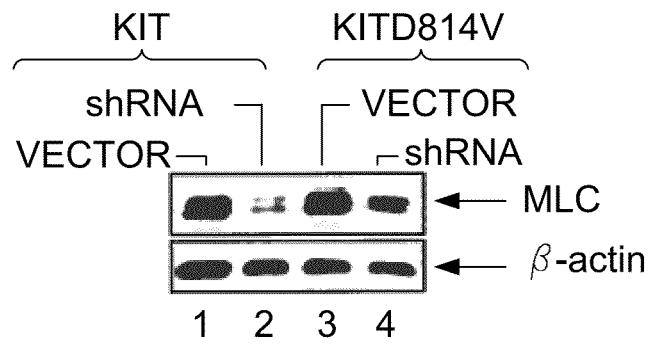
FIG. 9B is a Western blot assessing shRNA knockdown of myosin light chain (MLC) in cells expressing KIT and KITD814V as described in Example 8.
Figure 9C:
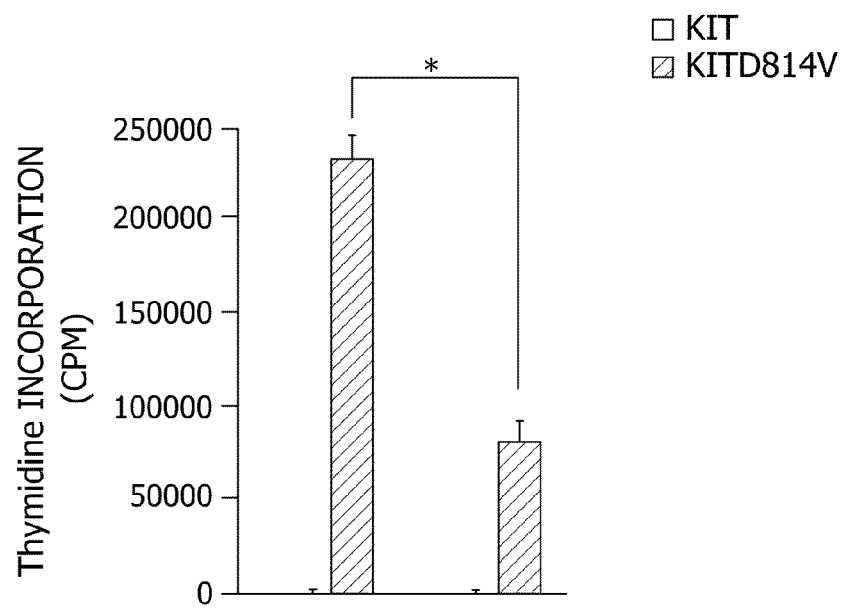
FIG. 9C is a graph showing thymidine incorporation in cells expressing KIT and KITD814V and co-infected with shRNA for knockdown of myosin light chain as described in Example 8.
Figure 9D:
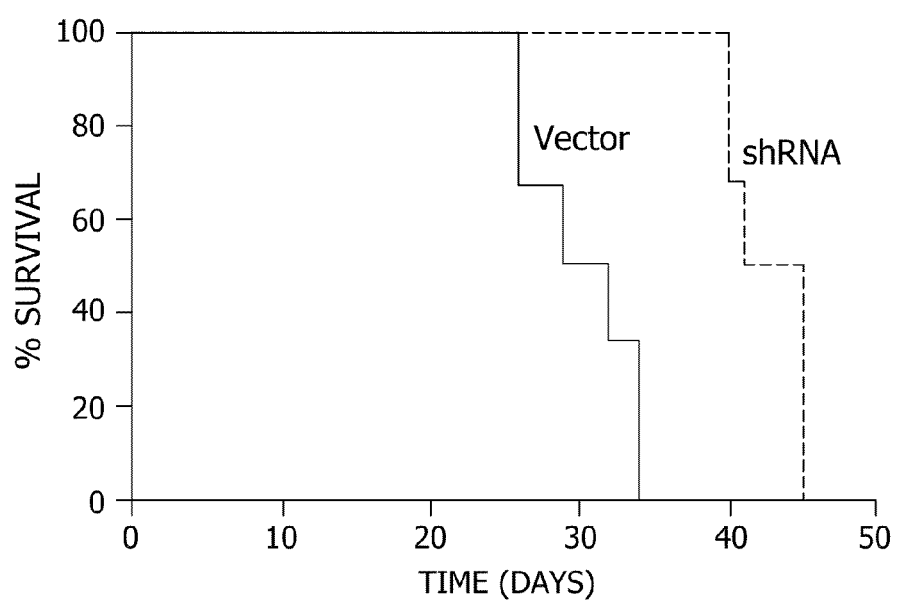
FIG. 9D is a graph showing percent survival of mice transplanted with cells expressing KIT and KITD814V and co-infected with shRNA for knockdown of myosin light chain as described in Example 8.
Figure 9E:
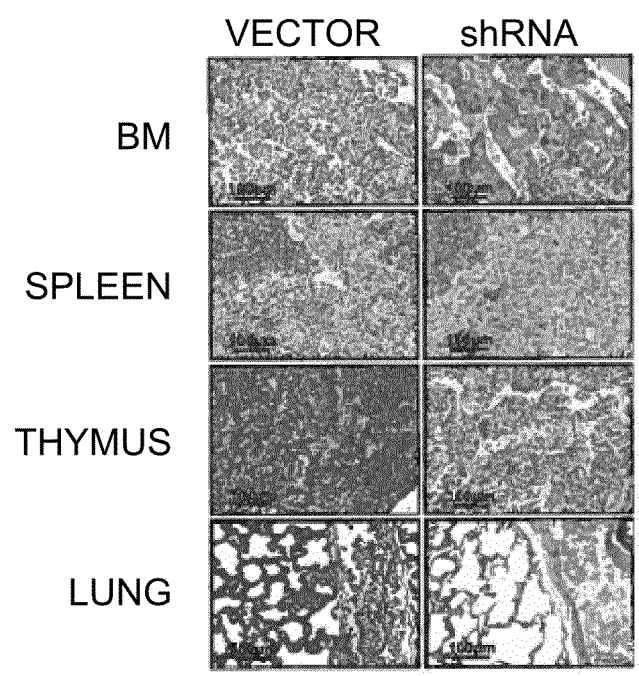
FIG. 9E are photographs showing histopathological analysis of bone marrow (BM), spleen, thymus, and lung from mice transplanted with cells expressing KIT and KITD814V and co-infected with shRNA for knockdown of myosin light chain as described in Example 8.

To investigate the role of MLC in MPD, MLC expression was knocked down using shRNA in cells bearing KIT or KITD814V. FIG. 9B shows significantly reduced expression of MLC in shRNA bearing cells compared to scrambled vector bearing cells. In addition, cells bearing KITD814V and shRNA showed a significant reduction in constitutive growth compared to cells bearing KITD814V and scrambled vector (FIG. 9C). Furthermore, mice transplanted with cells co-infected with KITD814V and shRNA survived significantly longer compared to mice bearing cells co-infected with KITD814V and scrambled vector (40-45 vs. 26-34 days, *p<0.05, FIG. 9D). Histopathological analysis of bone marrow, spleen, thymus and lungs from transplanted mice showed significantly increased infiltration of tumor cells in mice transplanted with cells co-infected with KITD814V and scrambled vector compared to KITD814V and shRNA (FIG. 9E). In contrast, mice transplanted with cells co-infected with KIT and scrambled vector or shRNA did not die and showed no signs of MPD (data not shown). These results demonstrate in vitro and in vivo involvement of MLC in KITD814V induced MPD downstream from ROCK.

To further understand the mechanism behind cell death in ROCK inhibitor treated oncogene bearing cells, F-actin content in 32D cells bearing KIT or KITD814V treated with or without H-1152 was measured. Cells bearing KIT showed minimal F-actin in the absence of growth factors. In contrast, cells bearing KITD814V showed constitutive F-actin in the absence of growth factors which was repressed by H-1152 treatment. Treatment of cells bearing KIT with H-1152 showed no effect on F-actin content in the presence of IL-3. These results suggest that inhibition of ROCK in KITD814V bearing cells but not in normal cells results in dephosphorylation of MLC, actin filament destabilization and disruption of cytoskeleton leading to cell death. Similar findings were observed when these same cells were treated with actin polymerization inhibitor cytochalasin D (data not shown).

Figure 9F:
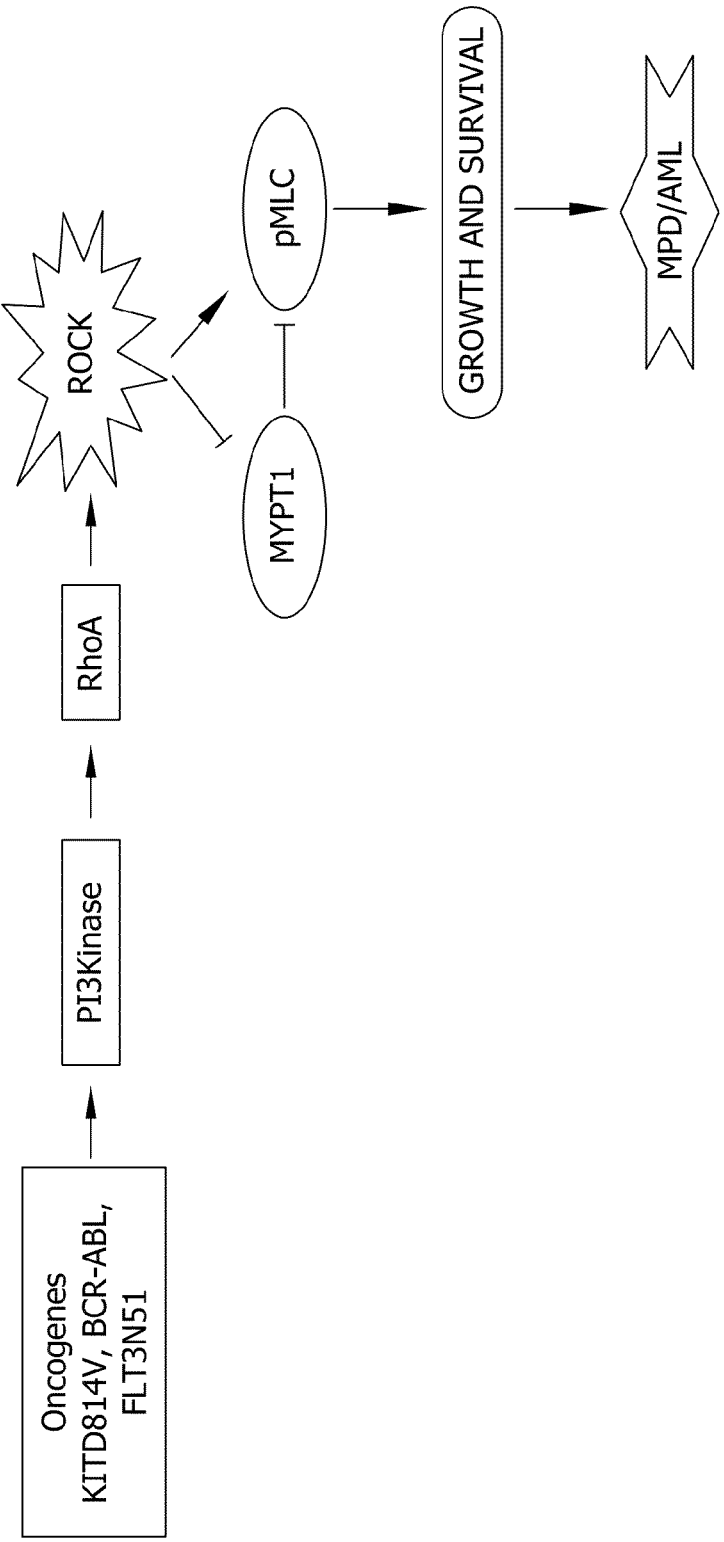
FIG. 9F is an illustration showing the KITD814V, BCR-ABL, and FLT3N51 oncogenes/PI3 kinase/Rho/ROCK signaling pathway.

The results presented above provide in vitro and in vivo genetic, biochemical as well as pharmacologic evidence suggesting that ROCK plays an essential role in regulating transformation via oncogenic forms of KIT, FLT3 as well as BCR-ABL. Collectively, these results identify PI3K/RhoA/ROCK/MLC pathway in regulating hematologic malignancies via the activating mutations of KIT, FLT3 and BCR-ABL (FIG. 9F). The results further demonstrate that treatment of KITD814V expressing cells with C3 exoenzyme (a Rho inhibitor) not only inhibits ROCK activation but also profoundly inhibits the growth of oncogene bearing cells. Thus, ROCK inhibitors provide an alternative strategy for treating hematologic malignancies in which ROCK is constitutively activated.

Using a mouse model of KITD814V or FLT3N51 driven MPD and treatment with H-1152 or fasudil suggests that inhibiting ROCK in vivo in oncogene bearing cells is of potential therapeutic significance. H-1152 or fasudil treated mice showed no signs of toxicity, which is consistent with previous studies demonstrating lack of toxicity upon ROCK inhibition in vivo using fasudil in human trials for cardiovascular indications. Based on these observations, along with our genetic studies demonstrating that constitutive growth of KITD814V bearing cells in the setting of ROCK1 deficient BM cells is normalized, targeting ROCK for treatment of hematologic malignancies due to activating mutations of KIT, FLT3 and BCR-ABL is likely to be a viable therapeutic option.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of treating a hematologic malignancy in an individual, the method comprising administering a myosin light chain-specific inhibitory RNA molecule of SEQ ID NO: 1.

2. The method of claim 1, wherein the hematologic malignancy is associated with a mutation of a gene selected from the group consisting of ROCK, KIT, FLT3, BCR-ABL, MLL-AF9 and MPLW515L.

3. The method of claim 1, wherein the myosin light chain-specific inhibitory RNA molecule of SEQ ID NO: 1 is selected from the group consisting of a siRNA and a shRNA.

4. The method of claim 1, wherein the individual is selected from the group consisting of a human, a mouse, a rat, a pig, a dog, a sheep and a non-human primate.

* * * * *

SEQUENCE LISTING

<160> NUMBER OF SEQ ID NOS: 3

<210> SEQ ID NO 1
<211> LENGTH: 29
<212> TYPE: DNA
<213> ORGANISM: Artificial Sequence
<220> FEATURE:
<223> OTHER INFORMATION: Synthetic

<400> SEQUENCE: 1
cgcgcaacct ccaatgtgtt cgccatgtt                                 29

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
gggctagcca gagtcatcag gaatgattcg                                30

<210> SEQ ID NO 3
<211> LENGTH: 30
<212> TYPE: DNA
<213> ORGANISM: Artificial Sequence

```
-continued

<220> FEATURE:
<223> OTHER INFORMATION: Synthetic

<400> SEQUENCE: 3
cgaatcattc ctgatgactc tggctagccc                                        30
```